US007786260B1

(12) United States Patent
Doidge et al.

(10) Patent No.: US 7,786,260 B1
(45) Date of Patent: Aug. 31, 2010

(54) POLYPEPTIDE FRAGMENTS COMPRISING C TERMINAL PORTION OF HELICOBACTER CATALASE

(75) Inventors: Christopher Vincent Doidge, Box Hill (AU); Elizabeth Ann Webb, Eltham (AU); Linda Joy Rothel, Glen Huntly (AU); Phillip Sutton, Sutherland (AU); Stuart Lloyd Hazell, Toowoomba (AU)

(73) Assignees: CSL Limited, Parkville, Victoria (AU); The University of New South Wales, Kensington, New South Wales (AU)

( * ) Notice: Subject to any disclaimer, the term of this patent is extended or adjusted under 35 U.S.C. 154(b) by 1548 days.

(21) Appl. No.: 10/110,628

(22) PCT Filed: Oct. 13, 2000

(86) PCT No.: PCT/AU00/01249

§ 371 (c)(1),
(2), (4) Date: Sep. 26, 2002

(87) PCT Pub. No.: WO01/29198

PCT Pub. Date: Apr. 26, 2001

(30) Foreign Application Priority Data

Oct. 15, 1999 (AU) .................................. PQ3471

(51) Int. Cl.
*C07K 14/195* (2006.01)
*A61K 39/00* (2006.01)
(52) U.S. Cl. .................. 530/350; 424/184.1; 424/234.1
(58) Field of Classification Search ........................ None
See application file for complete search history.

(56) References Cited

U.S. PATENT DOCUMENTS 6,005,090 A * 12/1999 Doidge et al. .............. 536/23.5
6,080,556 A * 6/2000 Sugiyama et al. .......... 435/69.1
6,468,545 B1 * 10/2002 Doidge et al. ............ 424/234.1
6,551,779 B1 * 4/2003 Sugiyama et al. ............. 435/6
6,630,582 B1 * 10/2003 Doidge et al. .............. 536/23.6
6,762,295 B2 * 7/2004 Doidge et al. .............. 536/23.7

(Continued)

FOREIGN PATENT DOCUMENTS

EP 0745674 * 4/1996

(Continued)

OTHER PUBLICATIONS

Odenbreit, Stephan et al, Journal of Bacteriology, vol. 178(23), pp. 6960-6967, Dec. 1996, Cloning and genetic characterization of Helicobacter pylori catalase and construction of a catalase deficient mutant strain.*

(Continued)

*Primary Examiner*—Robert B Mondesi
*Assistant Examiner*—Ginny Portner
(74) *Attorney, Agent, or Firm*—Foley & Lardner LLP

(57) ABSTRACT

An isolated polypeptide and immunogenic fragments thereof are described together with their variants and derivatives as novel immunogenic agents for treating or preventing *Helicobacter* infection in a mammalian host. The polypeptide comprises a C-terminal portion of a *Helicobacter* catalase, which portion lacks significant amino acid sequence identity with human catalase, wherein the polypeptide is other than full-length *Helicobacter* catalase.

15 Claims, 1 Drawing Sheet

U.S. PATENT DOCUMENTS

| | | | |
|---|---|---|---|
| 6,916,615 B2* | 7/2005 | Legrain et al. | 435/6 |
| 2002/0146423 A1* | 10/2002 | Doidge et al. | 424/184.1 |
| 2004/0052799 A1* | 3/2004 | Smith et al. | 424/184.1 |
| 2005/0063987 A1* | 3/2005 | Knapp et al. | 424/190.1 |

FOREIGN PATENT DOCUMENTS

| | | | |
|---|---|---|---|
| EP | 0 745 674 A2 | | 12/1996 |
| WO | WO 95/33482 A1 | | 12/1995 |
| WO | 97/19098 | * | 5/1997 |
| WO | 98/04702 | * | 2/1998 |
| WO | WO 98/06853 A1 | | 2/1998 |
| WO | 98/18323 | * | 5/1998 |
| WO | 98/24475 | * | 6/1998 |
| WO | WO 98/43478 A1 | | 10/1998 |

OTHER PUBLICATIONS

Miura, Hiromi e tal, Journal of Autoimmunity, 2000, vol. 15, pp. 433-440.*

Odenbreit, Stefan et al, Journal of Bacteriology, vol. 178(23), pp. 6960-6967, Dec. 1996, Cloning and Genetic Characterization of Helicobacter pylori catalase and contruction of a catalase deficient mutant strain.*

Guy, B et al, Immunology Letters, vol. 96(2005) pp. 261-275, Do Th1 or Th2 sequence motifs exist in proteins? Identification of amphipatic imunomodulatory domains in Helicobacter pylori catalase.*

Hocking et al., "Isolation of recombinant protective helicobacter pylori antigens," *Infection and Immunity*, Sep. 1999, pp. 4713-4719, vol. 67, No. 9.

Odenbreit et al., "Cloning and Genetic Characterization of Helicobacter pylori Catalase and Construction of a Catalase-Deficient Mutant Strain," *Journal of Bacteriology*, Dec. 1996, pp. 6960-6967, vol. 178, No. 23.

Radcliff et al., "Catalase, a Novel Antigen for Helicobacter Pylori Vaccination," *Infection and Immunity*, pp. 4668-4674, Nov. 1997, vol. 65, No. 11.

Sutton et al., "Review article: Helicobacter pylori vaccines: The current status," *Alimentary Pharmacology & Therapeutics*, Sep. 2000, pp. 1107-1118, vol. 14, No. 9, Blackwell Scientific Publications Ltd., Cambridge, GB.

* cited by examiner

POLYPEPTIDE FRAGMENTS COMPRISING C TERMINAL PORTION OF HELICOBACTER CATALASE

FIELD OF THE INVENTION

This invention relates generally to *Helicobacter* antigens. More particularly, the present invention relates to novel polypeptide fragments of *Helicobacter* catalase, particularly *Helicobacter pylori* catalase, and to the use of these fragments for treatment and prevention of gastroduodenal disease associated with *H. pylori* infection.

BACKGROUND OF THE INVENTION

*Helicobacter pylori* is a bacterium that infects the stomach lining (or gastric mucosa) of perhaps half the world's population. Spiral organisms were first microscopically observed in human gastric mucosa in 1906. However, *H. pylori* was not successfully cultured until 1982. Infection with the organism is usually chronic, and results in continuing inflammation of the gastric mucosa. The infection is often asymptomatic. However, in association with other cofactors, a proportion of infected people go on to develop sequelae including peptic ulceration of the stomach or duodenum, gastric adenocarcinomas and gastric lymphomas. Peptic ulcer treatment studies have shown that cure of *H. pylori* infection is associated with a dramatic reduction in the relapse rate of this usually chronic disease. Long term infection with *H. pylori* leads to the development of chronic atrophic gastritis, which has long been recognised as a precursor lesion in the development of gastric cancer. Thus, a number of studies have linked preceding *H. pylori* infection with an increased risk of developing gastric cancer. Therefore, eradication of current infection and prevention of new infection with this organism has the potential to significantly reduce the incidence of diseases that result in considerable morbidity and mortality (In *Helicobacter pylori* Biology and Clinical Practice. 1993. Edited by C. Stewart Goodwin and Bryan W. Worsley. Published by CRC Press; Halter et al 1992, *Yale J. Biol. Med.*, 65:625-638).

Infection with *H. pylori* is difficult to treat. Current experimental therapies for treating the infection have problems with efficacy and significant levels of adverse effects. There are no prophylactic measures clinically available. A solution to both the prevention and treatment of *H. pylori* infection would be the development of an immunogenic preparation that, as an immunotherapeutic, treats established infections, and as a vaccine, prevents the establishment of new or recurrent infections. Such a preparation would need to induce effective immune responses to protective antigens, while avoiding induction of responses to self-antigens or other potentially harmful immune responses. This may be achieved by identifying the specific protective component or components and formulating immunotherapeutic or vaccine preparations including such component(s).

The identification of such protective components of an organism is often accomplished using an animal model of the infection. Initially, there was no animal model available of human *H. pylori* infection. However, one such model was developed using a closely related organism, *H. felis*, and specific pathogen free (SPF) mice (Lee et al, 1990, *Gastroenterology*, 99: 1316-1323). This organism is able to colonise the gastric mucosa of SPF mice, where it establishes a chronic infection with many of the features of *H. pylori* infection in humans. *H. felis* infection in these mice induces a chronic gastritis and a raised immune response. As in the human case, this response is not effective in curing the infection.

The above model has been used to demonstrate that oral treatment of *H. felis* infected mice with a preparation containing disrupted *H. pylori* cells and cholera toxin as a mucosal adjuvant can cure a significant number of the infected mice (Doidge et al, 1994, *Lancet* 343(i): 914-915. This effect is likely to be mediated through an immune response to cross-reactive antigens possessed by each of the closely related *Helicobacter* species. Two such cross-reactive antigens have been identified by Doidge et al (WO 95/33482) as the microbial enzymes urease (Clayton et al, 1990, *Nucleic Acid Res.*, 18(2): 362) and catalase (Westblom et al, 1992, *Eur. J. of Clin. Microbiol. Infect. Dis.*, 11: 522-526).

Recently, an *H. pylori* (Sydney strain)/mouse model of human *H. pylori* infection has been developed and used by the present inventors to confirm that catalase, in particular recombinant catalase, has utility as a protective antigen. However, despite this encouraging finding, *Helicobacter* catalase may not be seriously considered as a therapeutic vaccine candidate due to its high homology with human catalase and associated potential to induce autoimmune disease.

SUMMARY OF THE INVENTION

The present invention arises from the unexpected discovery of a C-terminal portion of *Helicobacter* catalase, which lacks significant amino acid sequence identity with human catalase and which can elicit a protective or therapeutic immune response against *Helicobacter* species. Based on its sparse sequence identity with human catalase, this C-terminal portion is predicted to have significantly reduced potential for causing autoimmune disease.

Accordingly, in one aspect of the invention, there is provided an isolated polypeptide or immunogenic fragment thereof, or variant or derivative of these, for treating or preventing *Helicobacter* infection in a mammalian host, said polypeptide comprising a C-terminal portion of a *Helicobacter* catalase which portion lacks significant amino acid sequence identity with human catalase, wherein said polypeptide excludes full-length *Helicobacter* catalase.

Preferably, the *Helicobacter* catalase is a *Helicobacter pylori* catalase.

Suitably, said C-terminal portion comprises the sequence set forth in any one of SEQ ID NO: 2 or 4.

Preferably, said variant has at least 70% sequence identity to the amino acid sequence set forth in any one of SEQ ID NO: 2 or 4.

Suitably, the variant has at least 75%, preferably at least 80% and more preferably at least 85% sequence identity to the amino acid sequence set forth in any one of SEQ ID NO: 2 or 4.

In a preferred embodiment, said polypeptide lacks significant amino acid sequence identity with human catalase.

In another aspect, the invention provides a composition for use in treating or preventing *Helicobacter* infection in a mammalian host, comprising a polypeptide, immunogenic fragment, variant or derivative as broadly described above, together with a pharmaceutically acceptable carrier and/or diluent.

Suitably, said composition further comprises an adjuvant. Preferably, the adjuvant is a mucosal adjuvant.

Suitably, the composition further comprises at least one additional immunogen.

In yet another aspect of the invention, there is provided a method for treating or preventing *Helicobacter* infection in a mammalian host, comprising administering to said host an immunogenically effective amount of at least one immunogen selected from the group consisting of the polypeptide, immunogenic fragment, variant and derivative as broadly described above.

In one embodiment, the at least one immunogen is administered intranasally, orally or intragastrically, or any combination thereof.

In another aspect, the invention extends to use of at least one immunogen selected from the group consisting of the polypeptide, immunogenic fragment, variant and derivative as broadly described above in the manufacture of a medicament for treating or preventing *Helicobacter* infection in a mammalian host.

In yet another aspect, the invention contemplates a preparation for use in the treatment or prevention of *Helicobacter* infection in a mammalian host, comprising a vector which expresses an immunogen selected from the group consisting of a polypeptide, immunogenic fragment, variant and derivative as broadly described above.

In another aspect, the invention encompasses use of a preparation as broadly described above in the manufacture of a medicament for treating or preventing *Helicobacter* infection in a mammalian host.

According to still yet another aspect, the invention provides an isolated polynucleotide encoding a polypeptide, immunogenic fragment, variant or derivative as broadly described above.

Preferably, said polynucleotide comprises the sequence set forth in any one of SEQ ID NO: 1 or 3 or a polynucleotide variant thereof.

In one embodiment, the polynucleotide variant has at least 60%, preferably at least 70%, more preferably at least 80%, and still more preferably at least 90% sequence identity to the polynucleotide set forth in any one of SEQ ID NO: 1 or 3.

In another embodiment, the polynucleotide variant is capable of hybridising to the polynucleotide identified by SEQ ID NO: 1 or 3 under at least low stringency conditions, preferably under at least medium stringency conditions, and more preferably under high stringency conditions.

In a further aspect, the invention features a vector comprising a polynucleotide as broadly described above wherein the polynucleotide is operably linked to a regulatory polynucleotide.

In yet a further aspect, the invention provides a host cell containing said vector.

In still yet a further aspect of the invention there is provided a method of producing a recombinant polypeptide as broadly described above, comprising expressing the polynucleotide as broadly described above in a host cell.

In a still further aspect, the invention extends to the use of a polypeptide, immunogenic fragment, variant or derivative according to the present invention to produce an antigen-binding molecule that binds specifically to a C-terminal portion of a *Helicobacter* catalase.

In another aspect, the invention provides an antigen-binding molecule produced by the above method.

In yet another aspect, the invention provides a method of detecting *Helicobacter* in a biological sample suspected of containing it, comprising:

isolating the biological sample from a patient;
mixing the above-mentioned antigen-binding molecule with the biological sample to form a mixture; and
detecting specifically bound antigen-binding molecule in the mixture which indicates the presence of *Helicobacter*.

The invention further contemplates a method for diagnosing infection of patients by *Helicobacter*, comprising:

contacting a biological sample from a patient with a polypeptide, immunogenic fragment, variant or derivative according to the present invention; and
determining the presence or absence of a complex between said polypeptide, immunogenic fragment, variant or derivative and *Helicobacter*-specific antibodies in said sample, wherein the presence of said complex is indicative of said infection.

The invention also extends to the use of the polypeptide, immunogenic fragment, variant or derivative according to the present invention or to the use of the antigen-binding molecule mentioned above in a kit for detecting *Helicobacter* bacteria in a biological sample.

In a further aspect, the invention provides a method of identifying an immunogenic fragment of a polypeptide or variant according to the first mentioned aspect, comprising:

producing a fragment of said polypeptide or variant;
administering said fragment to a mammal; and
detecting an immune response in said mammal which response includes production of elements which specifically bind *Helicobacter* and which have a protective and/or therapeutic effect against *Helicobacter* infection.

In yet a further aspect, the invention contemplates a method of producing a variant of a C-terminal portion of a *Helicobacter* catalase or immunogenic fragment thereof which portion lacks significant amino acid sequence identity with human catalase, including the steps of:

combining a compound suspected of being said variant with at least one antigen-binding molecule that binds to said C-terminal portion or said immunogenic fragment; and
detecting a conjugate comprising said compound and said antigen-binding molecule wherein presence of the conjugate is indicative that said compound is said variant.

In yet another aspect, the invention extends to a method of producing a polypeptide variant of a parent polypeptide comprising the sequence set forth in any one of SEQ ID NO: 2 or 4, or an immunogenic fragment thereof, comprising:

combining a modified polypeptide whose sequence is distinguished from the parent polypeptide by substitution, deletion and/or addition of at least one amino acid with at least one antigen-binding molecule that binds to said C-terminal portion or said immunogenic fragment; and
detecting a conjugate comprising said modified polypeptide and said antigen-binding molecule wherein presence of the conjugate is indicative that said modified polypeptide is said variant.

DETAILED DESCRIPTION OF THE INVENTION

1. Definitions

Figure 1:
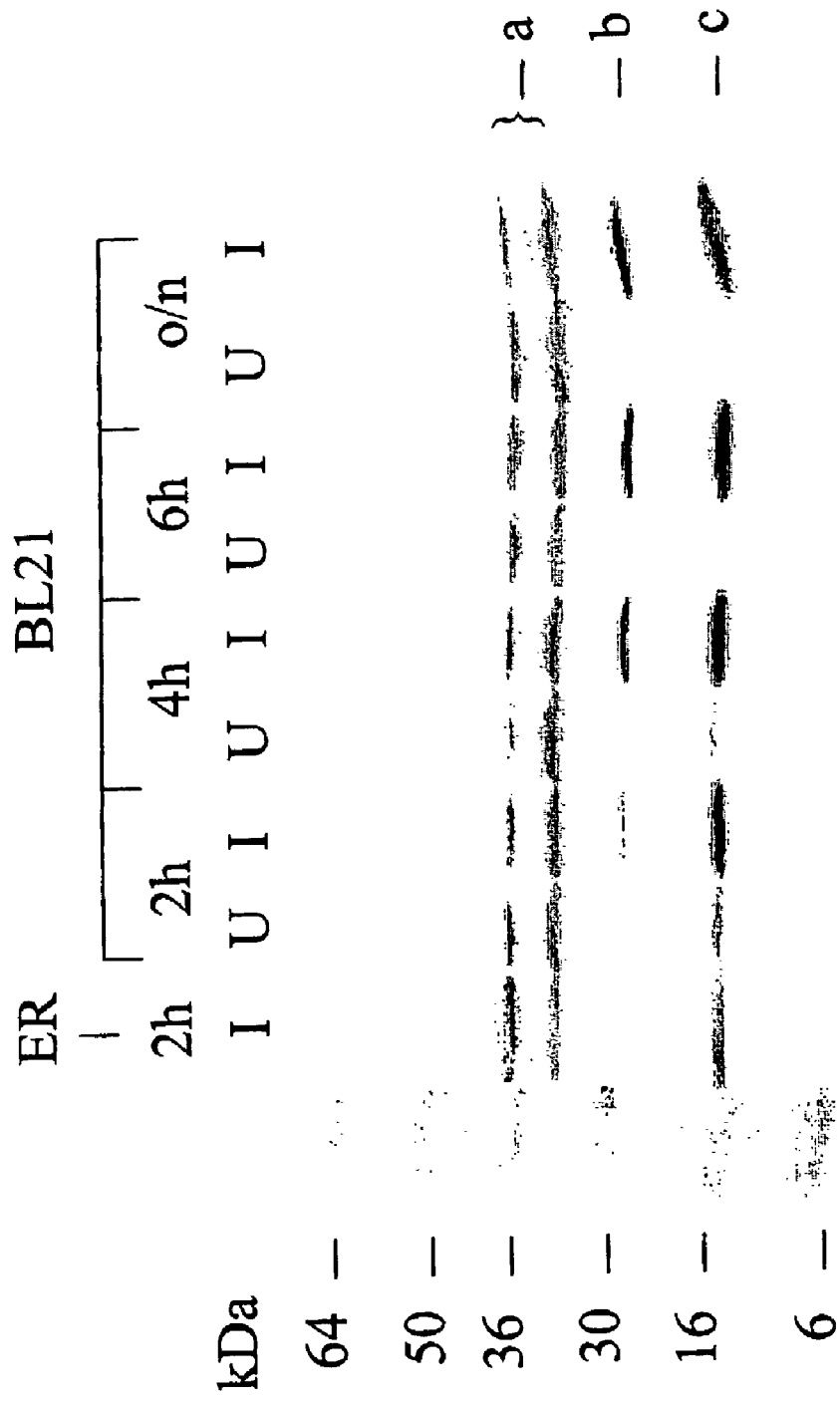
FIG. 1 shows a Western blot of cell extracts containing a recombinant polypeptide comprising a 134-aa C-terminal portion of *H. pylori* catalase, and incubated with monoclonal antibody CA5-8B8-1F3 raised against full-length *H. pylori* catalase. Each lane contained 20 μL of a whole cell suspension at $A_{600}$=4. ER, *E. coli* ER1793; a, *E. coli* cross-reactivity; I, Induced expression; b, Possible dimer; U, Uninduced expression, c, Catalase fragment (17 kDa).

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

The term "about" is used herein to refer to sequences that vary by as much as 30%, preferably by as much as 20% and more preferably by as much as 10% to the length of a reference sequence.

"Amplification product" refers to a nucleic acid product generated by nucleic acid amplification techniques.

By "antigen-binding molecule" is meant a molecule that has binding affinity for a target antigen. It will be understood that this term extends to immunoglobulins, immunoglobulin fragments and non-immunoglobulin derived protein frameworks that exhibit antigen-binding activity.

By "attenuated viral hosts" is meant viral vectors that either are naturally, or have been rendered, substantially avirulent.

The term "biological sample" as used herein refers to a sample that may be extracted, untreated, treated, diluted or concentrated from a patient. Suitably, the biological sample is selected from the group consisting of whole blood, serum, plasma, saliva, urine, sweat, ascitic fluid, peritoneal fluid, synovial fluid, amniotic fluid, cerebrospinal fluid, skin biopsy, and the like.

Throughout this specification, unless the context requires otherwise, the words "comprise", "comprises" and "comprising" will be understood to imply the inclusion of a stated step or element or group of steps or elements but not the exclusion of any other step or element or group of steps or elements.

By "corresponds to" or "corresponding to" is meant (a) a polynucleotide having a nucleotide sequence that is substantially identical or complementary to all or a portion of a reference polynucleotide sequence or encoding an amino acid sequence identical to an amino acid sequence in a peptide or protein; or (b) a peptide or polypeptide having an amino acid sequence that is substantially identical to a sequence of amino acids in a reference peptide or protein.

By "derivative" is meant a polypeptide that has been derived from the basic sequence by modification, for example by conjugation or complexing with other chemical moieties or by post-translational modification techniques as would be understood in the art. The term "derivative" also includes within its scope alterations that have been made to a parent sequence including additions, or deletions that provide for functional equivalent molecules. Accordingly, the term derivative encompasses molecules that will elicit an immune response against *Helicobacter* and preferably *H. pylori*.

For the purposes of the present invention, the phrase "elicit(s) an immune response" refers to the ability of the aforementioned polypeptide, immunogenic fragment or variant to produce an immune response in a mammal to which it is administered, wherein the response includes the production of elements which specifically bind *Helicobacter*, and/or which provide a protective or therapeutic effect against *Helicobacter* infection.

"Homology" refers to the percentage number of amino acids that are identical or constitute conservative substitutions as defined in TABLE A infra. Homology may be determined using sequence comparison programs such as GAP (Deveraux et al. 1984, *Nucleic Acids Research* 12, 387-395). In this way, sequences of a similar or substantially different length to those cited herein might be compared by insertion of gaps into the alignment, such gaps being determined, for example, by the comparison algorithm used by GAP.

"Hybridisation" is used herein to denote the pairing of complementary nucleotide sequences to produce a DNA-DNA hybrid or a DNA-RNA hybrid. Complementary base sequences are those sequences that are related by the base-pairing rules. In DNA, A pairs with T and C pairs with G. In RNA U pairs with A and C pairs with G. In this regard, the terms "match" and "mismatch" as used herein refer to the hybridisation potential of paired nucleotides in complementary nucleic acid strands. Matched nucleotides hybridise efficiently, such as the classical A-T and G-C base pair mentioned above. Mismatches are other combinations of nucleotides that do not hybridise efficiently.

By "immunogenic fragment" is meant a fragment of a full-length parent polypeptide which fragment elicits an immune response against *Helicobacter*, and preferably against *H. pylori*. For example, in the case of an immunogenic fragment of a polypeptide according to SEQ ID NO: 2 or 4, the polypeptide fragment must elicit an immune response, preferably a protective or therapeutic immune response, against *Helicobacter* infection. As used herein, the term "immunogenic fragment" includes deletion mutants and small peptides, for example of at least six, preferably at least 8 and more preferably at least 20 contiguous amino acids, which comprise antigenic determinants or epitopes. Several such fragments, for example encoding B and/or T cell epitopes, may be joined together. Peptides of this type may be obtained through the application of standard recombinant nucleic acid techniques or synthesised using conventional liquid or solid phase synthesis techniques. For example, reference may be made to solution synthesis or solid phase synthesis as described, for example, in Chapter 9 entitled "*Peptide Synthesis*" by Atherton and Shephard which is included in a publication entitled "*Synthetic Vaccines*" edited by Nicholson and published by Blackwell Scientific Publications. Alternatively, peptides can be produced by digestion of a polypeptide of the invention with proteinases such as endoLys-C, endoArg-C, endoGlu-C and *staphylococcus* V8-protease. The digested fragments can be purified by, for example, high performance liquid chromatographic (HPLC) techniques.

By "immunologically effective amount", in the context of the treatment or prevention of *Helicobacter* infection, is meant the administration of that amount to an individual host, either in a single dose or as part of a series, that is effective for treatment or prevention of *Helicobacter* infection. The effective amount will vary depending upon the health and physical condition of the individual to be treated or immunised, the taxonomic group of individual to be treated, the capacity of the individual's immune system to elicit an immune response (inclusive of a humoral and/or a cellular immune response), the degree of protection desired, the formulation of the vaccine, the assessment of the medical situation, and other relevant factors. It is expected that the amount will fall in a relatively broad range that can be determined through routine trials.

By "isolated" is meant material that is substantially or essentially free from components that normally accompany it in its native state. For example, an "isolated polynucleotide", as used herein, refers to a polynucleotide, which has been purified from the sequences which flank it in a naturally occurring state, e.g., a DNA fragment which has been removed from the sequences which are normally adjacent to the fragment.

By "lacking substantial amino acid sequence identity" is meant an amino acid sequence that has less than 70%, preferably less than 60%, more preferably less than 50% and even more preferably less than 40% sequence identity to a reference sequence. The window of comparison preferably spans the entire length of the amino acid sequence. Thus, the phrase "a portion of *Helicobacter* catalase lacking substantial amino acid sequence identity with human catalase" as used herein refers to a portion of a *Helicobacter* catalase that has less than 70%, preferably less than 60%, more preferably less than 50% and even more preferably less than 40% sequence identity to a corresponding C-terminal portion of human catalase.

By "obtained from" is meant that a sample such as, for example, a nucleic acid extract is isolated from, or derived from, a particular source of the host. For example, the nucleic acid extract may be obtained from tissue isolated directly from the host.

The term "oligonucleotide" as used herein refers to a polymer composed of a multiplicity of nucleotide units (deoxyribonucleotides or ribonucleotides, or related structural variants or synthetic analogues thereof) linked via phosphodiester bonds (or related structural variants or synthetic analogues thereof). Thus, while the term "oligonucleotide" typically refers to a nucleotide polymer in which the nucleotides and linkages between them are naturally occurring, it will be understood that the term also includes within its scope various analogues including, but not restricted to, peptide nucleic acids (PNAs), phosphoramidates, phosphorothioates, methyl phosphonates, 2-O-methyl ribonucleic acids, and the like. The exact size of the molecule may vary depending on the particular application. An oligonucleotide is typically rather short in length, generally from about 10 to 30 nucleotides, but the term can refer to molecules of any length, although the term "polynucleotide" or "nucleic acid" is typically used for large oligonucleotides.

By "operably linked" is meant that transcriptional and translational regulatory nucleic acids are positioned relative to a polypeptide-encoding polynucleotide in such a manner that the polynucleotide is transcribed and the polypeptide is translated.

The term "patient" refers to patients of human or other animal origin and includes any individual it is desired to examine or treat using the methods of the invention. However, it will be understood that "patient" does not imply that symptoms are present.

By "pharmaceutically-acceptable carrier and/or diluent" is meant a solid or liquid filler, diluent or encapsulating substance that may be safely used in topical or systemic administration.

The term "polynucleotide" or "nucleic acid" as used herein designates mRNA, RNA, cRNA, cDNA or DNA. The term typically refers to oligonucleotides greater than 30 nucleotides in length.

The terms "polynucleotide variant" and "variant" refer to polynucleotides displaying substantial sequence identity with a reference polynucleotide sequence or polynucleotides that hybridise with a reference sequence under stringent conditions that are defined hereinafter. Thus, a "polynucleotide variant" or "variant" refers to a polynucleotide whose sequence is distinguished from a reference polynucleotide by substitution, deletion and/or addition of at least one nucleotide. For example, it is well understood in the art that certain alterations inclusive of mutations, additions, deletions and substitutions can be made to a reference polynucleotide whereby the altered polynucleotide retains the biological function or activity of the reference polynucleotide. The terms "polynucleotide sequence variant" and "variant" also include naturally occurring allelic variants.

"Polypeptide", "peptide" and "protein" are used interchangeably herein to refer to a polymer of amino acid residues and to variants and synthetic analogues of the same. Thus, these terms apply to amino acid polymers in which one or more amino acid residues is a synthetic non-naturally occurring amino acid, such as a chemical analogue of a corresponding naturally occurring amino acid, as well as to naturally-occurring amino acid polymers.

The term "polypeptide variant" refers to a polypeptide whose sequence is distinguished from a reference polypeptide by substitution of at least one amino acid. For example, it is well understood in the art that some amino acids may be changed to others with broadly similar properties without changing the nature of the activity of a reference polypeptide (conservative substitutions) as described hereinafter. Accordingly, polypeptide variants as used herein encompass polypeptides that will elicit an immune response against *Helicobacter* and preferably *H. pylori*.

By "primer" is meant an oligonucleotide which, when paired with a strand of DNA, is capable of initiating the synthesis of a primer extension product in the presence of a suitable polymerising agent. The primer is preferably single-stranded for maximum efficiency in amplification but may alternatively be double-stranded. A primer must be sufficiently long to prime the synthesis of extension products in the presence of the polymerisation agent. The length of the primer depends on many factors, including application, temperature to be employed, template reaction conditions, other reagents, and source of primers. For example, depending on the complexity of the target sequence, the oligonucleotide primer typically contains 15 to 35 or more nucleotides, although it may contain fewer nucleotides. Primers can be large polynucleotides, such as from about 200 nucleotides to several kilobases or more. Primers may be selected to be "substantially complementary" to the sequence on the template to which it is designed to hybridise and serve as a site for the initiation of synthesis. By "substantially complementary", it is meant that the primer is sufficiently complementary to hybridise with a target nucleotide sequence. Preferably, the primer contains no mismatches with the template to which it is designed to hybridise but this is not essential. For example, non-complementary nucleotides may be attached to the 5'-end of the primer, with the remainder of the primer sequence being complementary to the template. Alternatively, non-complementary nucleotides or a stretch of non-complementary nucleotides can be interspersed into a primer, provided that the primer sequence has sufficient complementarity with the sequence of the template to hybridise therewith and thereby form a template for synthesis of the extension product of the primer.

"Probe" refers to a molecule that binds to a specific sequence or sub-sequence or other moiety of another molecule. Unless otherwise indicated, the term "probe" typically refers to a polynucleotide probe that binds to another nucleic acid, often called the "target nucleic acid", through complementary base pairing. Probes may bind target nucleic acids lacking complete sequence complementarity with the probe, depending on the stringency of the hybridisation conditions. Probes can be labelled directly or indirectly.

The term "recombinant polynucleotide" as used herein refers to a polynucleotide formed in vitro by the manipulation of nucleic acid into a form not normally found in nature. For example, the recombinant polynucleotide may be in the form of an expression vector. Generally, such expression vectors include transcriptional and translational regulatory nucleic acid operably linked to the nucleotide sequence.

By "recombinant polypeptide" is meant a polypeptide made using recombinant techniques, i.e., through the expression of a recombinant polynucleotide.

Terms used to describe sequence relationships between two or more polynucleotides or polypeptides include "reference sequence", "comparison window", "sequence identity", "percentage of sequence identity" and "substantial identity". A "reference sequence" is at least 6 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of typically 12 contiguous residues that is compared to a reference sequence. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerised implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (ie., resulting in the highest percentage homology over the comparison window) generated by any of the various methods selected. Reference also may be made to the BLAST family of programs as for example disclosed by Altschul et al., 1997, *Nucl. Acids Res.* 25:3389. A detailed discussion of sequence analysis can be found in Unit 19.3 of Ausubel et al., "Current Protocols in Molecular Biology", John Wiley & Sons Inc, 1994-1998, Chapter 15.

The term "sequence identity" as used herein refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by the DNASIS computer program (Version 2.5 for windows; available from Hitachi Software engineering Co., Ltd., South San Francisco, Calif., USA) using standard defaults as used in the reference manual accompanying the software.

"Stringency" as used herein, refers to the temperature and ionic strength conditions, and presence or absence of certain organic solvents, during hybridisation and washing procedures. The higher the stringency, the higher will be the degree of complementarity between immobilised target nucleotide sequences and the labelled probe polynucleotide sequences that remain hybridised to the target after washing.

The term "stringent conditions" as used herein refers to temperature and ionic conditions under which only nucleotide sequences having a high frequency of complementary bases will hybridise. The stringency required is nucleotide sequence dependent and depends upon the various components present during hybridisation. Generally, stringent conditions are selected to be about 10 to 20° C. lower than the thermal melting point $(T_m)$ for the specific sequence at a defined ionic strength and pH. The $T_m$ is the temperature (under defined ionic strength and pH) at which 50% of a target sequence hybridises to a complementary probe.

By "substantially avirulent" is meant a virus whose infectivity has been destroyed. Ideally, the infectivity of the virus is destroyed without affecting the proteins that carry the immunogenicity of the virus.

The term "substantially pure" as used herein describes a compound, e.g., a peptide that has been separated from components that naturally accompany it. Typically, a compound is substantially pure when at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides, by chromatography, gel electrophoresis or HPLC analysis. A compound, e.g., a polypeptide is also substantially purified when it is essentially free of naturally associated components when it is separated from the native contaminants which accompany it in its natural state.

By "target antigen" is meant an antigen that is associated with *Helicobacter* infection for which treatment or diagnosis is sought.

By "vector" is meant a nucleic acid molecule, preferably a DNA molecule derived, for example, from a plasmid, bacteriophage, or plant virus, into which a nucleic acid sequence may be inserted or cloned. A vector preferably contains one or more unique restriction sites and may be capable of autonomous replication in a defined host cell including a target cell or tissue or a progenitor cell or tissue thereof, or be integrable with the genome of the defined host such that the cloned sequence is reproducible. Accordingly, the vector may be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. A vector system may comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. The vector may also include a selection marker such as an antibiotic resistance gene that can be used for selection of suitable transformants. Examples of such resistance genes are well known to those of skill in the art.

2. Polypeptides of the Invention 2.1. C-Terminal Portion Polypeptides of *Helicobacter* Catalase The present invention provides an isolated or substantially pure polypeptide for treating or preventing *Helicobacter* infection in a mammalian host, comprising a C-terminal portion of a *Helicobacter* catalase which portion lacks significant amino acid sequence identity with human catalase, wherein said polypeptide excludes full-length *Helicobacter* catalase.

In a preferred embodiment, the *Helicobacter* catalase is a *Helicobacter pylori* catalase. For example, the C-terminal portion may comprise from about residue 358 through about residue 505 of full-length *H. pylori* catalase strain RU-1 disclosed under Accession No. AAC16068 of the GenPept database (National Center for Biotechnology Information). In this instance, the said C-terminal portion preferably comprises the sequence set forth in SEQ ID NO: 2. SEQ ID NO: 2 corresponds to a 134-aa fragment of full-length *H. pylori* catalase strain RU-1 spanning residue 372 through residue 505 of the full-length *H. pylori* catalase mentioned above. Preferably, the said C-terminal portion comprises the sequence set forth in SEQ ID NO: 4, which corresponds to a 134-aa fragment of full-length catalase from *H. pylori* strain HP921023.

2.2. Identification of Immunogenic Fragments

Immunogenic fragments may be identified according to any suitable procedure known in the art. For example, a suitable method may include producing a fragment of a polypeptide according to any one of SEQ ID NO: 2 or 4, administering the fragment to a mammal, and detecting an immune response in the mammal. Such response will include production of elements that specifically bind *Helicobacter* and/or provide a protective or therapeutic effect against *Helicobacter* infection.

Prior to testing a particular fragment for immunoreactivity in the above method, a variety of predictive methods may be used to deduce whether a particular fragment can be used to obtain an antibody that cross-reacts with the native antigen. These predictive methods may be based on amino-terminal or carboxy-terminal sequences as for example described in Chapter 11.14 of Ausubel et al., (1994-1998, supra). Alternatively, these predictive methods may be based on predictions of hydrophilicity as for example described by Kyte and Doolittle (1982, *J. Mol. Biol.* 157:105-132) and Hopp and Woods (1983, *Mol. Immunol.* 20:483-489), or predictions of secondary structure as for example described by Choo and Fasman (1978, *Ann. Rev. Biochem.* 47:251-276).

Generally, peptide fragments consisting of 10 to 15 residues provide optimal results. Peptides as small as 6 or as large as 20 residues have worked successfully. Such peptide fragments may then be chemically coupled to a carrier molecule such as keyhole limpet hemocyanin (KLH) or bovine serum albumin (BSA) as for example described in Chapters 11.14 and 11.15 of Ausubel et al., (1994-1998, supra). However, it will be understood that larger peptides may be desirable for eliciting a cellular immune response.

The peptides may be used to immunise an animal as for example discussed above. Antibody titres against the native or parent polypeptide from which the peptide was selected may then be determined by radioimmunoassay or ELISA as for instance described in Chapters 11.16 and 114 of Ausubel et al., (1994-1998, supra).

Antibodies may then be purified from a suitable biological fluid of the animal by ammonium sulphate fractionation or by chromatography as is well known in the art. Exemplary protocols for antibody purification are given in Chapters 10.11 and 11.13 of Ausubel et al., (1994-1998, supra). Immunoreactivity of the antibody against the native or parent polypeptide may be determined by any suitable procedure including, but not restricted to, western blot, enzyme-linked immunosorbent assay (ELISA) and radioimmunoassay (RIA).

2.3. Polypeptide Variants

The invention also contemplates polypeptide variants of a *Helicobacter* catalase C-terminal portion or fragment thereof according to the invention wherein said variants elicit an immune response against *Helicobacter* and preferably against *H. pylori*. In general, variants will be at least 75% homologous, more suitably at least 80%, preferably at least 85%, and more preferably at least 90% homologous to a natural C-terminal portion of a *Helicobacter* catalase as for example shown in any one of SEQ ID NO: 2 or 4. It is preferred that variants display at least 60%, more suitably at least 70%, preferably at least 75%, more preferably at least 80%, more preferably at least 85%, more preferably at least 90% and still more preferably at least 95% sequence identity with a polypeptide as for example shown in any one of SEQ ID NO: 2 or 4, or immunogenic fragments thereof. In this respect, the window of comparison preferably spans about the full length of the polypeptide or of the immunogenic fragment.

Suitably, the polypeptide variants of the invention will cross-react with or mimic immunologically an epitope of a *Helicobacter* catalase, preferably an epitope of a C-terminal portion of a *Helicobacter* catalase. Thus, polypeptide variants according to the invention may bind an antigen-binding molecule that also binds an epitope of a *Helicobacter* catalase, preferably an epitope in a C-terminal portion of a *Helicobacter* catalase.

Suitable polypeptide variants may be identified by combining a compound suspected of being a variant with at least one antigen-binding molecule that binds to the said C-terminal portion or immunogenic fragment. If a conjugate is formed comprising the compound and the antigen-binding molecule, this is indicative that the compound is a variant of the aforementioned C-terminal portion or immunogenic fragment.

In another embodiment, the polypeptide variant may be identified by combining a modified polypeptide whose sequence is distinguished from the parent polypeptide by substitution, deletion and/or addition of at least one amino acid with at least one antigen-binding molecule that binds to the C-terminal portion or said immunogenic fragment, and detecting a conjugate comprising the modified polypeptide and the antigen-binding molecule. When the conjugate is detected, this is indicative that the modified polypeptide is a said variant.

2.3.1. Assay Formats

Any suitable technique for determining formation of the conjugate may be used. For example, the antigen-binding molecule may be utilised in conventional immunoassays. Such immunoassays may include, but are not limited to, radioimmunoassays (RIAs), enzyme-linked immunosorbent assays (ELISAs) and immunochromatographic techniques (ICTs) which are well known to those of skill in the art. For example, reference may be made to Coligan et al. ("CURRENT PROTOCOLS IN IMMUNOLOGY", John Wiley & Sons, Inc, 1995-1997), in which a variety of immunoassays are described that may be used in accordance with the present invention. In this regard, the invention contemplates any immunoassay that can detect the presence of a conjugate as herein described. For example, immunoassays may include competitive and non-competitive assays as understood in the art. Such immunoassays may be carried out in solution or, at least in part, on solid supports, e.g., microtiter plates, polystyrene beads, nitrocellulose membranes, glass fibre membranes, immunochromatographic strips, and the like. The two most common formats for immunoassays are competitive and non-competitive (sandwich) formats.

In a competitive format, an antigen-binding molecule such as a polyclonal or monoclonal antibody is bound to a solid support. This antibody is suitably capable of binding a polypeptide according to any one of SEQ ID NO: 2 or 4, or an immunogenic fragment thereof. A solution of antigen labelled to permit detection (e.g., a labelled polypeptide or immunogenic fragment) is allowed to compete with unlabelled antigen (e.g., a compound suspected of being a variant) for the solid phase antibody. The extent to which the labelled antigen is bound to the solid phase or is detected in the solution phase can be used as a measure of the presence of said conjugate.

In a non-competitive, or sandwich format, a polyclonal or preferably a monoclonal antibody is bound to a solid support. Such antibody is suitably capable of binding to a polypeptide according to any one of SEQ ID NO: 2 or 4, or to immunogenic fragment thereof. In the case of a polyclonal antibody bound to the solid support, the sample containing the suspected antigen (i.e., a compound suspected of being said variant) is allowed to contact the solid phase in order for the antigen to bind to the antibody on the solid phase. Typically, after an incubation step, the sample is separated from the solid phase, which is then washed and incubated in the presence of additional polyclonal antibody that has been labelled to permit detection. Subsequently, the unbound labelled antibody is separated from the solid phase and the amount of labelled antibody in either the solution phase or bound to the solid phase in an antibody:antigen:antibody sandwich is determined as a measure of the presence of said conjugate. In the case of a non-competitive format employing monoclonal antibodies, a pair of monoclonal antibodies is typically utilised, one bound to the solid support and the other labelled to permit detection. The use of monoclonal antibody pairs that recognise different epitopic sites on an antigen makes it possible to conduct simultaneous immunometric assays in which the antigen and labelled antibody incubations do not require the intermediate steps of prior processes.

Alternatively, solid phase detection of the conjugate may be determined by immunoaffinity chromatography, as for example described by Coligan et al., (supra, in particular Chapter 9.5) and Ausubel et al. ("CURRENT PROTOCOLS IN MOLECULAR BIOLOGY", John Wiley & Sons Inc, 1994-1998, in particular Chapter 10.11), by immunoblotting, as for example described by Ausubel et al. (supra, in Chapter 10.8), or by immunoprecipitation, as for example described by Ausubel et al. (supra, in Chapter 10.16).

Solution-phase immunoassays are also contemplated by the present invention. For instance, detection of said conjugate may be carried out in solution using flow cytometric analysis as for example described in Shapiro, H. M. ("PRACTICAL FLOW CYTOMETRY", $3^{rd}$ ed., Wiley-Liss, New York, 1995).

2.3.2. Methods of Producing Polypeptide Variants 2.3.2.1. Mutagenesis

Polypeptide variants according to the invention can be identified either rationally, or via established methods of mutagenesis (see, for example, Watson, J. D. et al., "MOLECULAR BIOLOGY OF THE GENE", Fourth Edition, Benjamin/Cummings, Menlo Park, Calif., 1987). Significantly, a random mutagenesis approach requires no a priori information about the gene sequence that is to be mutated. This approach has the advantage that it assesses the desirability of a particular mutant based on its function, and thus does not require an understanding of how or why the resultant mutant protein has adopted a particular conformation. Indeed, the random mutation of target gene sequences has been one approach used to obtain mutant proteins having desired characteristics (Leatherbarrow, R. 1986, *J. Prot. Eng.* 1:7-16; Knowles, J. R., 1987, *Science* 236:1252-1258; Shaw, W. V., 1987, *Biochem. J.* 246:1-17; Gerit, J. A. 1987, *Chem.*

*Rev.* 87:1079-1105). Alternatively, where a particular sequence alteration is desired, methods of site-directed mutagenesis can be employed. Thus, such methods may be used to selectively alter only those amino acids of the protein that are believed to be important (Craik, C. S., 1985, *Science* 228:291-297; Cronin, et al., 1988, *Biochem.* 27:4572-4579; Wilks, et al., 1988, *Science* 242:1541-1544).

Variant peptides or polypeptides, resulting from rational or established methods of mutagenesis or from combinatorial chemistries as hereinafter described, may comprise conservative amino acid substitutions. Exemplary conservative substitutions in an immunogenic polypeptide or polypeptide fragment according to the invention may be made according to the following table:

TABLE A

| Original Residue | Exemplary Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile, |
| Phe | Met, Leu, Tyr |
| Ser | Thr |
| Thr | Ser |
| Trp | Tyr |
| Tyr | Trp, Phe |
| Val | Ile, Leu |

Substantial changes in function are made by selecting substitutions that are less conservative than those shown in TABLE A. Other replacements would be non-conservative substitutions and relatively fewer of these may be tolerated. Generally, the substitutions which are likely to produce the greatest changes in a polypeptide's properties are those in which (a) a hydrophilic residue (eg, Ser or Thr) is substituted for, or by, a hydrophobic residue (eg, Ala, Leu, Ile, Phe or Val); (b) a cysteine or proline is substituted for, or by, any other residue; (c) a residue having an electropositive side chain (eg, Arg, His or Lys) is substituted for, or by, an electronegative residue (eg, Glu or Asp) or (d) a residue having a bulky side chain (eg, Phe or Trp) is substituted for, or by, one having a smaller side chain (eg, Ala, Ser) or no side chain (eg, Gly).

What constitutes suitable variants may be determined by conventional techniques. For example, nucleic acids encoding a polypeptide according to any one of SEQ ID NO: 2 or 4, or fragment thereof can be mutated using either random mutagenesis for example using transposon mutagenesis, or site-directed mutagenesis as described, for example, in Section 3.2 herein.

2.3.2.2. Peptide Libraries Produced by Combinatorial Chemistry

A number of facile combinatorial technologies can be utilised to synthesise molecular libraries of immense diversity. In the present case, variants of an immunogenic polypeptide, preferably an immunogenic polypeptide fragment according to the invention, can be synthesised using such technologies. Variants can be screened subsequently using the methods described in Section 2.3.1.

Preferably, soluble synthetic peptide combinatorial libraries (SPCLs) are produced which offer the advantage of working with free peptides in solution, thus permitting adjustment of peptide concentration to accommodate a particular assay system. SPCLs are suitably prepared as hexamers. In this regard, a majority of binding sites is known to involve four to six residues. Cysteine is preferably excluded from the mixture positions to avoid the formation of disulfides and more difficult-to-define polymers. Exemplary methods of producing SPCLs are disclosed by Houghten et al. (1991, *Nature* 354:84-86; 1992, *BioTechniques* 13:412-421), Appel et al. (1992, *Immunomethods* 1:17-23), and Pinilla et al. (1992, *BioTechniques* 13:901-905; 1993, *Gene* 128:71-76).

Preparation of combinatorial synthetic peptide libraries may employ either t-butyloxycarbonyl (t-Boc) or 9-fluorenylmethyloxycarbonyl (Fmoc) chemistries (see Chapter 9.1, of Coligan et al., supra; Stewart and Young, 1984, Solid Phase Peptide Synthesis, 2nd ed. Pierce Chemical Co., Rockford, Ill; and Atherton and Sheppard, 1989, Solid Phase Peptide Synthesis: A Practical Approach. IRL Press, Oxford) preferably, but not exclusively, using one of two different approaches. The first of these approaches, suitably termed the "split-process-recombine" or "split synthesis" method, was described first by Furka et al. (1988, 14*th Int. Congr. Biochem.*, Prague, Czechoslovakia 5:47; 1991, *Int. J. Pept. Protein Res.* 37:487-493) and Lam et al. (1991, *Nature* 354:82-84), and reviewed later by Eichler et al. (1995, *Medicinal Research Reviews* 15(6):481-496) and Balkenhohl et al. (1996, *Angew. Chem. Int. Ed. Engl.* 35:2288-2337). Briefly, the split synthesis method involves dividing a plurality of solid supports such as polymer beads into n equal fractions representative of the number of available amino acids for each step of the synthesis (e.g., 20 L-amino acids), coupling a single respective amino acid to each polymer bead of a corresponding fraction, and then thoroughly mixing the polymer beads of all the fractions together. This process is repeated for a total of x cycles to produce a stochastic collection of up to $N^x$ different compounds. The peptide library so produced may be screened with a suitably labelled monoclonal antibody. Upon detection, some of the positive beads are selected for sequencing to identify the active peptide. Such peptide may be subsequently cleaved from the beads, and assayed using the same antibody to identify the most active peptide sequence.

The second approach, the chemical ratio method, prepares mixed peptide resins using a specific ratio of amino acids empirically defined to give equimolar incorporation of each amino acid at each coupling step. Each resin bead contains a mixture of peptides. Approximate equimolar representation can be confirmed by amino acid analysis (Dooley and Houghten, 1993, *Proc. Natl. Acad. Sci. U.S.A.* 90:10811-10815; Eichler and Houghten, 1993, *Biochemistry* 32:11035-11041). Preferably, the synthetic peptide library is produced on polyethylene rods, or pins, as a solid support, as for example disclosed by Geysen et al. (1986, *Mol. Immunol.* 23:709-715). An exemplary peptide library of this type may consist of octapeptides in which the third and fourth position are defined with each of the 20 amino acids, whereas the remaining six positions are present as mixtures. This peptide library can be represented by the formula Ac-XXO$_1$O$_2$XXXX-S$_s$, where S$_s$ is the solid support. Peptide mixtures remain on the pins when assayed against a soluble receptor molecule.

2.32.3. Polypeptide or Peptide Libraries Produced by Phage Display

The identification of variants can also be facilitated through the use of a phage display protein ligand screening system as for example described by Lowman, et al. (1991, *Biochem.* 30:10832-10838), Markland, et al. (1991, *Gene* 109:13-19), Roberts, et al. (1992, *Proc. Natl. Acad. Sci.* (U.S.A.) 89:2429-2433), Smith, G. P. (1985, *Science* 228:1315-1317), Smith, et al. (1990, *Science* 248:1126-1128) and Lardner et al. (U.S. Pat. No. 5,223,409). In general, this method involves expressing a fusion protein in which the desired protein ligand is fused to the N-terminus of a viral coat protein (such as the M13 Gene III coat protein, or a lambda coat protein).

In one embodiment, a library of phage is engineered to display novel peptides within the phage coat protein sequences. Novel peptide sequences are generated by random mutagenesis of gene fragments encoding an immoreactive polypeptide fragment using error-prone PCR, or by in vivo mutation by *E. coli* mutator cells. The novel peptides displayed on the surface of the phage are placed in contact, with an antigen binding molecule such as an antibody or antibody fragment against the particular immunogenic polypeptide or polypeptide fragment on which the novel peptide sequences are based. Phage that display coat protein having peptides that are capable of binding to such antibodies are immobilised by such treatment, whereas all other phage can be washed away. After the removal of unbound phage, the bound phage can be amplified, and the DNA encoding their coat proteins can be sequenced. In this manner, the amino acid sequence of the embedded peptide or polypeptide can be deduced.

2.32.4. Rational Drug Design

Variants of naturally occurring immunogenic polypeptides or polypeptide fragments according to the invention may also be obtained using the principles of conventional or of rational drug design as for example described by Andrews, et al. (In: "PROCEEDINGS OF THE ALFRED BENZON SYMPOSIUM", volume 28, pp. 145-165, Munksgaard, Copenhagen, 1990), McPherson, A. (1990, *Eur. J. Biochem.* 189:1-24), Hol, et al. (In: "MOLECULAR RECOGNITION: CHEMICAL AND BIOCHEMICAL PROBLEMS", Roberts, S. M. (ed.); Royal Society of Chemistry; pp. 84-93, 1989), Hol, W. G. J. (1989, *Arzneim-Forsch.* 39:1016-1018), Hol, W. G. J. (1986, *Agnew Chem. Int. Ed. Engl.* 25:767-778).

In accordance with the methods of conventional drug design, the desired variant molecules are obtained by randomly testing molecules whose structures have an attribute in common with the structure of a "native" immunogenic polypeptide or polypeptide fragment according to the invention. The quantitative contribution that results from a change in a particular group of a binding molecule can be determined by measuring the capacity of competition or cooperativity between the native immunogenic polypeptide or polypeptide fragment and the putative polypeptide variant.

In one embodiment of rational drug design, the polypeptide variant is designed to share an attribute of the most stable three-dimensional conformation of an immunogenic polypeptide or polypeptide fragment according to the invention. Thus, the variant may be designed to possess chemical groups that are oriented in a way sufficient to cause ionic, hydrophobic, or van der Waals interactions that are similar to those exhibited by the immunogenic polypeptide or polypeptide fragment. In a second method of rational design, the capacity of a particular immunogenic polypeptide or polypeptide fragment to undergo conformational "breathing" is exploited. Such "breathing"—the transient and reversible assumption of a different molecular conformation—is a well-appreciated phenomenon, and results from temperature, thermodynamic factors, and from the catalytic activity of the molecule. Knowledge of the 3-dimensional structure of the immunogenic polypeptide or polypeptide fragment facilitates such an evaluation. An evaluation of the natural conformational changes of an immunogenic polypeptide or polypeptide fragment facilitates the recognition of potential hinge sites, potential sites at which hydrogen bonding, ionic bonds or van der Waals bonds might form or might be eliminated due to the breathing of the molecule, etc. Such recognition permits the identification of the additional conformations that the immunogenic polypeptide or polypeptide fragment could assume, and enables the rational design and production of immunomimetics that share such conformations.

The preferred method for performing rational immunomimetic design employs a computer system capable of forming a representation of the three-dimensional structure of the immunogenic polypeptide or polypeptide fragment (such as those obtained using RIBBON (Priestle, J., 1988, *J. Mol. Graphics.* 21:572), QUANTA (Polygen), InSite (Biosyn), or Nanovision (American Chemical Society)). Such analyses are exemplified by Hol, et al. (In: "MOLECULAR RECOGNITION: CHEMICAL AND BIOCHEMICAL PROBLEMS", supra, Hol, W. G. J. (1989, supra) and Hol, W. G. J., (1986, supra).

In lieu of such direct comparative evaluations of putative polypeptide variants, screening assays may be used to identify such molecules. Such assays will preferably exploit the capacity of the variant to bind to an antigen-binding molecule as described in Section 2.3.1.

2.4. Polypeptide Derivatives

With reference to suitable derivatives of the invention, such derivatives include amino acid deletions and/or additions to a C-terminal portion of a *Helicobacter* catalase or fragment thereof or variant of these, wherein said derivatives elicit an immune response against *Helicobacter* and preferably against *H. pylori*. "Additions" of amino acids may include fusion of the polypeptides, immunogenic fragments and polypeptide variants of the invention with other polypeptides or proteins. For example, it will be appreciated that said polypeptides, immunogenic fragments or variants may be incorporated into larger polypeptides, and that such larger polypeptides may also be expected to elicit an immune response against *Helicobacter* and preferably against *H. pylori*.

The polypeptides, immunogenic fragments or variants of the invention may be fused to a further protein, for example, which is not derived from the original host. The further protein may assist in the purification of the fusion protein. For instance, a polyhistidine tag or a maltose binding protein may be used in this respect as described in more detail below. Alternatively, it may produce an immune response, which is effective against *Helicobacter*, or it may produce an immune response against another pathogen. Other possible fusion proteins are those which produce an immunomodulatory response. Particular examples of such proteins include Protein A or glutathione S-transferase (GST).

Other derivatives contemplated by the invention include, but are not limited to, modification to side chains, incorporation of unnatural amino acids and/or their derivatives during peptide, polypeptide or protein synthesis and the use of crosslinkers and other methods which impose conformational constraints on the polypeptides, fragments and variants of the invention.

Examples of side chain modifications contemplated by the present invention include modifications of amino groups such as by acylation with acetic anhydride; acylation of amino groups with succinic anhydride and tetrahydrophthalic anhydride; amidination with methylacetimidate; carbamoylation of amino groups with cyanate; pyridoxylation of lysine with pyridoxal-5-phosphate followed by reduction with NaBH$_4$; reductive alkylation by reaction with an aldehyde followed by reduction with NaBH$_4$; and trinitrobenzylation of amino groups with 2,4,6-trinitrobenzene sulphonic acid (TNBS).

The carboxyl group may be modified by carbodiimide activation via O-acylisourea formation followed by subsequent derivitization, by way of example, to a corresponding amide.

The guanidine group of arginine residues may be modified by formation of heterocyclic condensation products with reagents such as 2,3-butanedione, phenylglyoxal and glyoxal.

Sulfhydryl groups may be modified by methods such as performic acid oxidation to cysteic acid; formation of mercurial derivatives using 4-chloromercuriphenylsulphonic acid, 4-chloromercuribenzoate; 2-chloromercuri-4-nitrophenol, phenylmercury chloride, and other mercurials; formation of a mixed disulphides with other thiol compounds; reaction with maleimide, maleic anhydride or other substituted maleimide; carboxymethylation with iodoacetic acid or iodoacetamide; and carbamoylation with cyanate at alkaline pH.

Tryptophan residues may be modified, for example, by alkylation of the indole ring with 2-hydroxy-5-nitrobenzyl bromide or sulphonyl halides or by oxidation with N-bromosuccinimide.

Tyrosine residues may be modified by nitration with tetranitromethane to form a 3-nitrotyrosine derivative.

The imidazole ring of a histidine residue may be modified by N-carbethoxylation with diethylpyrocarbonate or by alkylation with iodoacetic acid derivatives.

Examples of incorporating unnatural amino acids and derivatives during peptide synthesis include but are not limited to, use of 4-amino butyric acid, 6-aminohexanoic acid, 4-amino-3-hydroxy-5-phenylpentanoic acid, 4-amino-3-hydroxy-6-methylheptanoic acid, t-butylglycine, norleucine, norvaline, phenylglycine, ornithine, sarcosine, 2-thienyl alanine and/or D-isomers of amino acids. A list of unnatural amino acids contemplated by the present invention is shown in TABLE B.

TABLE B

| Non-conventional amino acid | Non-conventional amino acid |
|---|---|
| α-aminobutyric acid | L-N-methylalanine |
| α-amino-α-methylbutyrate | L-N-methylarginine |
| aminocyclopropane-carboxylate | L-N-methylasparagine |
| aminoisobutyric acid | L-N-methylaspartic acid |
| aminonorbornyl-carboxylate | L-N-methylcysteine |
| cyclohexylalanine | L-N-methylglutamine |
| cyclopentylalanine | L-N-methylglutamic acid |
| L-N-methylisoleucine | L-N-methylhistidine |
| D-alanine | L-N-methylleucine |
| D-arginine | L-N-methyllysine |
| D-aspartic acid | L-N-methylmethionine |
| D-cysteine | L-N-methylnorleucine |
| D-glutamate | L-N-methylnorvaline |
| D-glutamic acid | L-N-methylornithine |
| D-histidine | L-N-methylphenylalanine |
| D-isoleucine | L-N-methylproline |
| D-leucine | L-N-medlylserine |
| D-lysine | L-N-methylthreonine |
| D-methionine | L-N-methyltryptophan |
| D-ornithine | L-N-methyltyrosine |
| D-phenylalanine | L-N-methylvaline |
| D-proline | L-N-methylethylglycine |
| D-serine | L-N-methyl-t-butylglycine |
| D-threonine | L-norleucine |
| D-tryptophan | L-norvaline |
| D-tyrosine | α-methyl-aminoisobutyrate |
| D-valine | α-methyl-γ-aminobutyrate |
| D-α-methylalanine | α-methylcyclohexylalanine |
| D-α-methylarginine | α-methylcylcopentylalanine |

TABLE B-continued

| Non-conventional amino acid | Non-conventional amino acid |
| --- | --- |
| D-α-methylasparagine | α-methyl-α-napthylalanine |
| D-α-methylaspartate | α-methylpenicillamine |
| D-α-methylcysteine | N-(4-aminobutyl)glycine |
| D-α-methylglutamine | N-(2-aminoethyl)glycine |
| D-α-methylhistidine | N-(3-aminopropyl)glycine |
| D-α-methylisoleucine | N-amino-α-methylbutyrate |
| D-α-methylleucine | α-napthylalanine |
| D-α-methyllysine | N-benzylglycine |
| D-α-methylmethionine | N-(2-carbamylediyl)glycine |
| D-α-methylornithiine | N-(carbamylmethyl)glycine |
| D-α-methylphenylalanine | N-(2-carboxyethyl)glycine |
| D-α-methylproline | N-(carboxymethyl)glycine |
| D-α-methylserine | N-cyclobutylglycine |
| D-α-methylthreonine | N-cycloheptylglycine |
| D-α-methyltryptophan | N-cyclohexylglycine |
| D-α-methyltyrosine | N-cyclodecylglycine |
| L-α-methylleucine | L-α-methyllysine |
| L-α-methylmethionine | L-α-methylnorleucine |
| L-α-methylnorvatine | L-α-methylornithine |
| L-α-methylphenylalanine | L-α-methylproline |
| L-α-methylserine | L-α-methylthreonine |
| L-α-methyltryptophan | L-α-methyltyrosine |
| L-α-methylvaline | L-N-methylhomophenylalanine |
| N-(N-(2,2-diphenylethyl carbamylmethyl)glycine | N-(N-(3,3-diphenylpropyl carbamylmethyl)glycine |
| 1-carbox-1-(2,2-diphenyl-ethyl amino)cyclopropane | |

The invention also extends to covalently modifying a polypeptide, fragment or variant of the invention with dinitrophenol, in order to render it immunogenic in humans.

Also contemplated is the use of crosslinkers, for example, to stabilise 3D conformations of the polypeptides or immunogenic fragments or variants of the invention, using homobifunctional cross linkers such as bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety or carbodiimide. In addition, peptides can be conformationally constrained, for example, by introduction of double bonds between $C_\alpha$ and $C_\beta$ atoms of amino acids, by incorporation of $C_\alpha$, and $N_\alpha$-methylamino acids, and by formation of cyclic peptides or analogues by introducing covalent bonds such as forming an amide bond between the N and C termini between two side chains or between a side chain and the N or C terminus of the peptides or analogues. For example, reference may be made to: Marlowe (1993, *Biorganic & Medicinal Chemistry Letters* 3:437-44) who describes peptide cyclisation on TFA resin using trimethylsilyl (TMSE) ester as an orthogonal protecting group; Pallin and Tam (1995, *J. Chem. Soc. Chem. Comm.* 2021-2022) who describe the cyclisation of unprotected peptides in aqueous solution by oxime formation; Algin et al (1994, *Tetrahedron Letters* 35: 9633-9636) who disclose solid-phase synthesis of head-to-tail cyclic peptides via lysine side-chain anchoring; Kates et al (1993, *Tetrahedron Letters* 34: 1549-1552) who describe the production of head-to-tail cyclic peptides by three-dimensional solid phase strategy, Tumelty et al (1994, *J. Chem. Soc. Chem. Comm.* 1067-1068) who describe the synthesis of cyclic peptides from an immobilised activated intermediate, wherein activation of the immobilised peptide is carried out with N-protecting group intact and subsequent removal leading to cyclisation; McMurray et al (1994, *Peptide Research* 7:195-206) who disclose head-to-tail cyclisation of peptides attached to insoluble supports by means of the side chains of aspartic and glutamic acid; Hruby et al (1994, *Reactive Polymers* 22:231-241) who teach an alternate method for cyclising peptides via solid supports; and Schmidt and Langer (1997, *J Peptide Res.* 49: 67-73) who disclose a method for synthesising cyclotetrapeptides and cyclopentapeptides. The foregoing methods may be used to produce conformationally constrained polypeptides that elicit an immune response against *Helicobacter* and preferably against *H. pylori*.

The invention also contemplates polypeptides, immunogenic fragments or variants of the invention that have been modified using ordinary molecular biological techniques so as to improve their resistance to proteolytic degradation or to optimise solubility properties or to render them more suitable as an immunogenic agent.

2.5. Methods of Preparing the Polypeptides of the Invention

Polypeptides of the inventions may be prepared by any suitable procedure known to those of skill in the art. For example, the polypeptides may be prepared by a procedure including the steps of:

preparing a recombinant polynucleotide comprising a nucleotide sequence encoding the polypeptide set forth in any one of SEQ ID NO: 2 or 4, or immunogenic fragment thereof, or variant or derivative of these, which nucleotide sequence is operably linked to a regulatory polynucleotide;

introducing the recombinant polynucleotide into a suitable host cell;

culturing the host cell to express recombinant polypeptide from said recombinant polynucleotide; and isolating the recombinant polypeptide.

Suitably said nucleotide sequence comprises the sequence set forth in any one of SEQ ID NO: 1 or 3.

The recombinant polynucleotide preferably comprises either an expression vector that may be a self-replicating extra-chromosomal vector such as a plasmid, or a vector that integrates into a host genome.

The regulatory polynucleotide will typically comprise transcriptional and translational initiation and termination sequences that will generally be appropriate for the host cell used for expression. Numerous types of appropriate expression vectors and suitable regulatory sequences are known in the art for a variety of host cells.

Typically, the regulatory polynucleotide includes, but is not limited to, promoter sequences, leader or signal sequences, ribosomal binding sites, transcriptional start and stop sequences, translational start and termination sequences, and enhancer or activator sequences.

Constitutive or inducible promoters as known in the art are contemplated by the invention. The promoters may be either naturally occurring promoters, or hybrid promoters that combine elements of more than one promoter.

In a preferred embodiment, the expression vector contains a selectable marker gene to allow the selection of transformed host cells. Selection genes are well known in the art and will vary with the host cell used. Preferably, the expression vector is pGEXStopIV™ as described more fully hereinafter.

The expression vector may also include a fusion partner (typically provided by the expression vector) so that the recombinant polypeptide of the invention is expressed as a fusion polypeptide with said fusion partner. The main advantage of fusion partners is that they assist identification and/or purification of said fusion polypeptide.

In order to express said fusion polypeptide, it is necessary to ligate a polynucleotide according to the invention into the expression vector so that the translational reading frames of the fusion partner and the polynucleotide coincide.

Well known examples of fusion partners include, but are not limited to, glutathione-S-transferase (GST), Fc potion of human IgG, maltose binding protein (MBP) and hexahistidine (HIS$_6$) (SEQ ID NO: 5), which are particularly useful for isolation of the fusion polypeptide by affinity chromatography. For the purposes of fusion polypeptide purification by affinity chromatography, relevant matrices for affinity chromatography are glutathione-, amylose-, and nickel- or cobalt-conjugated resins respectively. Many such matrices are available in "kit" form, such as the QIAexpress™ system (Qiagen) useful with (HIS$_6$) (SEQ ID NO: 5) fusion partners and the Pharmacia GST purification system.

Another fusion partner well known in the art is green fluorescent protein (GFP). This fusion partner serves as a fluorescent "tag" which allows the fusion polypeptide of the invention to be identified by fluorescence microscopy or by flow cytometry. The GFP tag is useful when assessing sub-cellular localisation of the fusion polypeptide of the invention, or for isolating cells which express the fusion polypeptide of the invention. Flow cytometric methods such as fluorescence activated cell sorting (FACS) are particularly useful in this latter application.

Preferably, the fusion partners also have protease cleavage sites, such as for Factor X$_a$ or Thrombin, which allow the relevant protease to partially digest the fusion polypeptide of the invention and thereby liberate the recombinant polypeptide of the invention therefrom. The liberated polypeptide can then be isolated from the fusion partner by subsequent chromatographic separation.

Fusion partners according to the invention also include within their scope "epitope tags", which are usually short peptide sequences for which a specific antibody is available. Well known examples of epitope tags for which specific monoclonal antibodies are readily available include c-Myc, influenza virus, hemagglutinin and FLAG tags.

The step of introducing into the host cell the recombinant polynucleotide may be effected by any suitable method including transfection, and transformation, the choice of which will be dependent on the host cell employed. Such methods are well known to those of skill in the art.

Recombinant polypeptides of the invention may be produced by culturing a host cell transformed with an expression vector containing nucleic acid encoding a polypeptide, immunogenic fragment, variant or derivative according to the invention. The conditions appropriate for protein expression will vary with the choice of expression vector and the host cell. This is easily ascertained by one skilled in the art through routine experimentation.

Suitable host cells for expression may be prokaryotic or eukaryotic. One preferred host cell for expression of a polypeptide according to the invention is a bacterium. The bacterium used may be *Escherichia coli* Alternatively, the host cell may be an insect cell such as, for example, SF9 cells that may be utilised with a baculovirus expression system.

The recombinant protein may be conveniently prepared by a person skilled in the art using standard protocols as for example described in Sambrook, et al., MOLECULAR CLONING. A LABORATORY MANUAL (Cold Spring Harbor Press, 1989), in particular Sections 16 and 17; Ausubel et al., CURRENT PROTOCOLS IN MOLECULAR BIOLOGY (John Wiley & Sons, Inc. 1994-1998), in particular Chapters 10 and 16; and Coligan et al., CURRENT PROTOCOLS IN PROTEIN SCIENCE (John Wiley & Sons, Inc. 1995-1997), in particular Chapters 1, 5 and 6.

In some cases, the recombinant polypeptide may require refolding. Methods of refolding are well known to those of skill in the art.

Alternatively, the polypeptides, polypeptide fragments, or variants or derivatives of the invention may be synthesised using solution synthesis or solid phase synthesis as described, for example, in Chapter 9 of Atherton and Shephard (supra).

3. Polynucleotides of the Invention 3.1. Polynucleotides Encoding C-Terminal Portion of *Helicobacter* Catalase The invention further provides a polynucleotide that encodes a polypeptide, immunogenic fragment, variant or derivative as defined above. Suitably, the polynucleotide comprises SEQ ID NO: 1. As will be more fully described hereinafter, SEQ ID NO: 1 corresponds to nucleotide 1365 through nucleotide 1769 of the *H. pylori* strain RU-1 catalase gene described under Accession No. U67458 of the National Center for Biotechnology Information Entrez database (supra). Preferably, the polynucleotide comprises SEQ ID NO: 3, which is derived from the catalase gene of *H. pylori* strain HP921023.

3.2. Polynucleotides Variants

In general, polynucleotide variants according to the invention comprise regions that show at least 60%, more suitably at least 70%, preferably at least 80%, and most preferably at least 90% sequence identity over a reference polynucleotide sequence of identical size ("comparison window") or when compared to an aligned sequence in which the alignment is performed by a computer homology program known in the art. What constitutes suitable variants may be determined by conventional techniques. For example, a polynucleotide according to any one of SEQ ID NO: 1 or 3 can be mutated using random mutagenesis (e.g., transposon mutagenesis), oligonucleotide-mediated (or site-directed) mutagenesis, PCR mutagenesis and cassette mutagenesis of an earlier prepared variant or non-variant version of an isolated natural promoter according to the invention.

Oligonucleotide-mediated mutagenesis is a preferred method for preparing nucleotide substitution variants of a polynucleotide of the invention. This technique is well known in the art as, for example, described by Adelman et al. (1983, *DNA* 2:183). Briefly, a DNA encoding a C-terminal portion of a *Helicobacter* catalase (e.g., SEQ ID NO: 1 or 3) is altered by hybridising an oligonucleotide encoding the desired mutation to a template DNA, where the template is the single-stranded form of a plasmid or bacteriophage containing the unaltered or native DNA sequence of said C-terminal portion. After hybridisation, a DNA polymerase is used to synthesise an entire second complementary strand of the template that will thus incorporate the oligonucleotide primer, and will code for the selected alteration in said C-terminal portion.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridise properly to the single-stranded DNA template molecule.

The DNA template can be generated by those vectors that are either derived from bacteriophage M13 vectors, or those vectors that contain a single-stranded phage origin of replication as described by Viera et al. (1987, *Methods Enzymol.* 153:3). Thus, the DNA that is to be mutated may be inserted into one of the vectors to generate single-stranded template. Production of single-stranded template is described, for example, in Sections 4.21-4.41 of Sambrook et al. (1989, supra).

Alternatively, the single-stranded template may be generated by denaturing double-stranded plasmid (or other DNA) using standard techniques.

For alteration of the native DNA sequence, the oligonucleotide is hybridised to the single-stranded template under suitable hybridisation conditions. A DNA polymerising enzyme, usually the Klenow fragment of DNA polymerase I, is then added to synthesise the complementary strand of the template using the oligonucleotide as a primer for synthesis. A heteroduplex molecule is thus formed such that one strand of DNA encodes the mutated form of the catalase C-terminal portion under test, and the other strand (the original template) encodes the native unaltered sequence of the catalase C-terminal portion under test. This heteroduplex molecule is then transformed into a suitable host cell, usually a prokaryote such as E. coli. After the cells are grown, they are plated onto agarose plates and screened using the oligonucleotide primer having a detectable label to identify the bacterial colonies having the mutated DNA. The resultant mutated DNA fragments are then cloned into suitable expression hosts such as E. coli using conventional technology and clones that retain the desired antigenic activity are detected. Where the clones have been derived using random mutagenesis techniques, positive clones would have to be sequenced in order to detect the mutation.

Alternatively, linker-scanning mutagenesis of DNA may be used to introduce clusters of point mutations throughout a sequence of interest that has been cloned into a plasmid vector. For example, reference may be made to Ausubel et al., supra, (in particular, Chapter 8.4) which describes a first protocol that uses complementary oligonucleotides and requires a unique restriction site adjacent to the region that is to be mutagenised. A nested series of deletion mutations is first generated in the region. A pair of complementary oligonucleotides is synthesised to fill in the gap in the sequence of interest between the linker at the deletion endpoint and the nearby restriction site. The linker sequence actually provides the desired clusters of point mutations as it is moved or "scanned" across the region by its position at the varied endpoints of the deletion mutation series. An alternate protocol is also described by Ausubel et al., supra, which makes use of site directed mutagenesis procedures to introduce small clusters of point mutations throughout the target region. Briefly, mutations are introduced into a sequence by annealing a synthetic oligonucleotide containing one or more mismatches to the sequence of interest cloned into a single-stranded M13 vector. This template is grown in an E. coli dut⁻ ung⁻ strain, which allows the incorporation of uracil into the template strand. The oligonucleotide is annealed to the template and extended with T4 DNA polymerase to create a double-stranded heteroduplex. Finally, the heteroduplex is introduced into a wild-type E. coli strain, which will prevent replication of the template strand due to the presence of apurinic sites (generated where uracil is incorporated), thereby resulting in plaques containing only mutated DNA.

Region-specific mutagenesis and directed mutagenesis using PCR may also be employed to construct polynucleotide variants according to the invention. In this regard, reference may be made, for example, to Ausubel et al., supra, in particular Chapters 8.2A and 8.5.

Alternatively, suitable polynucleotide sequence variants of the invention may be prepared according to the following procedure:
    obtaining a nucleic acid extract from a *Helicobacter* species;
    creating primers which are optionally degenerate wherein each comprises a portion of a reference polynucleotide encoding a C-terminal portion of a *Helicobacter* catalase, preferably encoding the sequence set forth in any one of SEQ ID NO: 2 or 4; and
    using said primers to amplify, via nucleic acid amplification techniques, at least one amplification product from said nucleic acid extract, wherein said amplification product corresponds to a polynucleotide variant.

Suitable nucleic acid amplification techniques are well known to the skilled addressee, and include polymerase chain reaction (PCR) as for example described in Ausubel et al. (supra); strand displacement amplification (SDA) as for example described in U.S. Pat. No. 5,422,252; rolling circle replication (RCR) as for example described in Liu et al., (1996, *J. Am. Chem. Soc.* 118:1587-1594 and International application WO 92/01813) and Lizardi et al., (International Application WO 97/19193); nucleic acid sequence-based amplification (NASBA) as for example described by Sooknanan et al., (1994, *Biotechniques* 17:1077-1080); and Q-β replicase amplification as for example described by Tyagi et al., (1996, *Proc. Natl. Acad. Sci. USA* 93:5395-5400).

Typically, polynucleotide variants that are substantially complementary to a reference polynucleotide are identified by blotting techniques that include a step whereby nucleic acids are immobilised on a matrix (preferably a synthetic membrane such as nitrocellulose), followed by a hybridisation step, and a detection step. Southern blotting is used to identify a complementary DNA sequence; northern blotting is used to identify a complementary RNA sequence. Dot blotting and slot blotting can be used to identify complementary DNA/DNA, DNA/RNA or RNA/RNA polynucleotide sequences. Such techniques are well known by those skilled in the art, and have been described in Ausubel et al. (1994-1998, supra) at pages 2.9.1 through 2.9.20.

According to such methods, Southern blotting involves separating DNA molecules according to size by gel electrophoresis, transferring the size-separated DNA to a synthetic membrane, and hybridising the membrane-bound DNA to a complementary nucleotide sequence labelled radioactively, enzymatically or fluorochromatically. In dot blotting and slot blotting, DNA samples are directly applied to a synthetic membrane prior to hybridisation as above.

An alternative blotting step is used when identifying complementary polynucleotides in a cDNA or genomic DNA library, such as through the process of plaque or colony hybridisation. A typical example of this procedure is described in Sambrook et al. ("Molecular Cloning. A Laboratory Manual", Cold Spring Harbour Press, 1989) Chapters 8-12.

Typically, the following general procedure can be used to determine hybridisation conditions. Polynucleotides are blotted/transferred to a synthetic membrane, as described above. A reference polynucleotide such as a polynucleotide of the invention is labelled as described above, and the ability of this labelled polynucleotide to hybridise with an immobilised polynucleotide is analysed.

A skilled addressee will recognise that a number of factors influence hybridisation. The specific activity of radioactively labelled polynucleotide sequence should typically be greater than or equal to about $10^8$ dpm/mg to provide a detectable signal. A radiolabeled nucleotide sequence of specific activity 108 to $10^9$ dpm/mg can detect approximately 0.5 pg of DNA. It is well known in the art that sufficient DNA must be immobilised on the membrane to permit detection. It is desirable to have excess immobilised DNA, usually 10 µg. Adding an inert polymer such as 10% (w/v) dextran sulfate (MW 500, 000) or polyethylene glycol 6000 during hybridisation can also increase the sensitivity of hybridisation (see Ausubel supra at 2.10.10).

To achieve meaningful results from hybridisation between a polynucleotide immobilised on a membrane and a labelled polynucleotide, a sufficient amount of the labelled polynucleotide must be hybridised to the immobilised polynucleotide following washing. Washing ensures that the labelled polynucleotide is hybridised only to the immobilised polynucleotide with a desired degree of complementarity to the labelled polynucleotide.

It will be understood that polynucleotide variants according to the invention will hybridise to a reference polynucleotide under at least low stringency conditions. Reference herein to low stringency conditions include and encompass from at least about 1% v/v to at least about 15% v/v formamide and from at least about 1 M to at least about 2 M salt for hybridisation at 42° C., and at least about 1 M to at least about 2 M salt for washing at 42° C. Low stringency conditions also may include 1% Bovine Serum Albumin (BSA), 1 mM EDTA, 0.5 M $NaHPO_4$ (pH 7.2), 7% SDS for hybridisation at 65° C., and (i) 2×SSC, 0.1% SDS; or (ii) 0.5% BSA, 1 mM EDTA, 40 mM $NaHPO_4$ (pH 7.2), 5% SDS for washing at room temperature.

Suitably, the polynucleotide variants hybridise to a reference polynucleotide under at least medium stringency conditions. Medium stringency conditions include and encompass from at least about 16% v/v to at least about 30% v/v formamide and from at least about 0.5 M to at least about 0.9 M salt for hybridisation at 42° C., and at least about 0.5 M to at least about 0.9 M salt for washing at 42° C. Medium stringency conditions also may include 1% Bovine Serum Albumin (BSA), 1 mM EDTA, 0.5 M $NaHPO_4$ (pH 7.2), 7% SDS for hybridisation at 65° C., and (i) 2×SSC, 0.1% SDS; or (ii) 0.5% BSA, 1 mM EDTA, 40 mM $NaHPO_4$ (pH 7.2), 5% SDS for washing at 42° C.

Preferably, the polynucleotide variants hybridise to a reference polynucleotide under high stringency conditions. High stringency conditions include and encompass from at least about 31% v/v to at least about 50% v/v formamide and from at least about 0.01 M to at least about 0.15 M salt for hybridisation at 42° C., and at least about 0.01 M to at least about 0.15 M salt for washing at 42° C. High stringency conditions also may include 1% BSA, 1 mM EDTA, 0.5 M $NaHPO_4$ (pH 7.2), 7% SDS for hybridisation at 65° C., and (i) 0.2×SSC, 0.1% SDS; or (ii) 0.5% BSA, 1 mM EDTA, 40 mM $NaHPO_4$ (pH 7.2), 1% SDS for washing at a temperature in excess of 65° C.

Other stringent conditions are well known in the art. A skilled addressee will recognise that various factors can be manipulated to optimise the specificity of the hybridisation. Optimisation of the stringency of the final washes can serve to ensure a high degree of hybridisation. For detailed examples, see Ausubel et al., supra at pages 2.10.1 to 2.10.16 and Sambrook et al. (1989, supra) at sections 1.101 to 1.104.

While stringent washes are typically carried out at temperatures from about 42° C. to 68° C., one skilled in the art will appreciate that other temperatures may be suitable for stringent conditions. Maximum hybridisation typically occurs at about 20° C. to 25° C. below the $T_m$ for formation of a DNA-DNA hybrid. It is well known in the art that the $T_m$ is the melting temperature, or temperature at which two complementary polynucleotide sequences dissociate. Methods for estimating $T_m$ are well known in the art (see Ausubel et al., supra at page 2.10.8).

In general, washing is carried out at T=69.3+0.41 (G+C) %−12° C. However, the $T_m$ of a duplex DNA decreases by 1° C. with every increase of 1% in the number of mismatched base pairs.

In a preferred hybridisation procedure, a membrane (e.g., a nitrocellulose membrane or a nylon membrane) containing immobilised DNA is hybridised overnight at 42° C. in a hybridisation buffer [50% deionised formamide, 5×SSC, 5×Denhardt's solution (0.1% ficoll, 0.1% polyvinylpyrrolidone and 0.1% bovine serum albumin), 0.1% SDS and 200 mg/mL denatured salmon sperm DNA)] containing labelled probe. The membrane is then subjected to two sequential medium stringency washes (i.e., 2×SSC/0.1% SDS for 15 min at 45° C., followed by 2×SSC/0.1% SDS for 15 min at 50° C.), followed by two sequential high stringency washes (i.e., 0.2×SSC/0.1% SDS for 12 min at 55° C. followed by 0.2×SSC and 0.1% SDS solution for 12 min).

Methods for detecting a labelled polynucleotide hybridised to an immobilised polynucleotide are well known to practitioners in the art. Such methods include autoradiography, phosphorimaging, and chemiluminescent, fluorescent and colorimetric detection.

4. Antigen-Binding Molecules

The invention also contemplates antigen-binding molecules against the aforementioned polypeptides, fragments, variants and derivatives. For example, the antigen-binding molecules may comprise whole polyclonal antibodies. Such antibodies may be prepared, for example, by injecting a polypeptide, fragment, variant or derivative of the invention into a production species, which may include mice or rabbits, to obtain polyclonal antisera. Methods of producing polyclonal antibodies are well known to those skilled in the art. Exemplary protocols which may be used are described for example in Coligan et al., CURRENT PROTOCOLS IN IMMUNOLOGY, (John Wiley & Sons, Inc, 1991), and Ausubel et al., (1994-1998, supra), in particular Section III of Chapter 11.

In lieu of the polyclonal antisera obtained in the production species, monoclonal antibodies may be produced using the standard method as described, for example, by Köhler and Milstein (1975, Nature 256, 495-497), or by more recent modifications thereof as described, for example, in Coligan et al., (1991, supra) by immortalising spleen or other antibody producing cells derived from a production species which has been inoculated with one or more of the polypeptides, fragments, variants or derivatives of the invention.

The invention also contemplates as antigen-binding molecules Fv, Fab, Fab' and F(ab')$_2$ immunoglobulin fragments.

Alternatively, the antigen-binding molecule may comprise a synthetic stabilised Fv fragment. Exemplary fragments of this type include single chain Fv fragments (sFv, frequently termed scFv) in which a peptide linker is used to bridge the N terminus or C terminus of a $V_H$ domain with the C terminus or N-terminus, respectively, of a $V_L$ domain. ScFv lack all constant parts of whole antibodies and are not able to activate complement. Suitable peptide linkers for joining the $V_H$ and $V_L$ domains are those which allow the $V_H$ and $V_L$ domains to fold into a single polypeptide chain having an antigen binding site with a three dimensional structure similar to that of the antigen binding site of a whole antibody from which the Fv fragment is derived. Linkers having the desired properties may be obtained by the method disclosed in U.S. Pat. No. 4,946,778. However, in some cases a linker is absent. ScFvs may be prepared, for example, in accordance with methods outlined in Krebber et al (1997, *J. Immunol. Methods;* 201(1):

35-55). Alternatively, they may be prepared by methods described in U.S. Pat. No. 5,091,513, European Patent No 239,400 or the articles by Winter and Milstein (1991, *Nature* 349:293) and Plückthun et al (1996, *In Antibody engineering: A practical approach.* 203-252).

Alternatively, the synthetic stabilised Fv fragment comprises a disulphide stabilised Fv (dsFv) in which cysteine residues are introduced into the $V_H$ and $V_L$ domains such that in the fully folded Fv molecule the two residues will form a disulphide bond therebetween. Suitable methods of producing dsFv are described for example in (Glockscuther et al. *Biochem.* 29: 1363-1367; Reiter et al. 1994, *J. Biol. Chem.* 269: 18327-18331; Reiter et al. 1994, *Biochem.* 33: 5451-5459; Reiter et al. 1994. Cancer Res. 54: 2714-2718; Webber et al. 1995, *Mol. Immunol.* 32: 249-258).

Also contemplated as antigen-binding molecules are single variable region domains (termed dAbs) as for example disclosed in (Ward et al. 1989, *Nature* 341: 544-546; Hamers-Casterman et al 1993, *Nature.* 363: 446-448; Davies & Riechmann, 1994, *FEBS Lett.* 339: 285-290).

Alternatively, the antigen-binding molecule may comprise a "minibody". In this regard, minibodies are small versions of whole antibodies, which encode in a single chain the essential elements of a whole antibody. Suitably, the minibody is comprised of the $V_H$ and $V_L$ domains of a native antibody fused to the hinge region and CH3 domain of the immunoglobulin molecule as, for example, disclosed in U.S. Pat. No. 5,837,821.

In an alternate embodiment, the antigen-binding molecule may comprise non-immunoglobulin derived, protein frameworks. For example, reference may be made to (Ku & Schultz, 1995, *Proc. Natl. Acad. Sci. USA,* 92: 652-6556) which discloses a four-helix bundle protein cytochrome b562 having two loops randomised to create complementarity determining regions (CDRs), which have been selected for antigen binding.

The antigen-binding molecule may be multivalent (i.e., having more than one antigen binding site). Such multivalent molecules may be specific for one or more antigens. Multivalent molecules of this type may be prepared by dimerisation of two antibody fragments through a cysteinyl-containing peptide as, for example disclosed by (Adams et al., 1993, *Cancer Res.* 53: 4026-4034; Cumber et al., 1992, *J. Immunol.* 149: 120-126). Alternatively, dimerisation may be facilitated by fusion of the antibody fragments to amphiphilic helices that naturally dimerise (Pack P. Plückthun, 1992, *Biochem.* 31: 1579-1584), or by use of domains (such as the leucine zippers jun and fos) that preferentially heterodimerise (Kostelny et al., 1992, *J. Immunol.* 148: 1547-1553). In an alternate embodiment, the multivalent molecule may comprise a multivalent single chain antibody (multi-scFv) comprising at least two scFvs linked together by a peptide linker. In this regard, non-covalently or covalently linked scFv dimers termed "diabodies" may be used. Multi-scFvs may be bispecific or greater depending on the number of scFvs employed having different antigen binding specificities. Multi-scFvs may be prepared for example by methods disclosed in U.S. Pat. No. 5,892,020.

The antigen-binding molecules of the invention may be used for affinity chromatography in isolating natural or recombinant *Helicobacter* catalase. For example reference may be made to immunoaffinity chromatographic procedures described in Chapter 9.5 of Coligan et al., (1995-1997, supra).

The antigen-binding molecules can be used to screen expression libraries for variant polypeptides of the invention. They can also be used to detect *Helicobacter* infection, preferably *H. pylori* infection, as described hereinafter.

5. Detection of *Helicobacter*

The presence or absence of *Helicobacter* in a patient may determined by isolating a biological sample from a patient, mixing an antigen-binding molecule described above with the biological sample to form a mixture, and detecting specifically bound antigen-binding molecule in the mixture which indicates the presence of *Helicobacter* in the sample.

Any suitable technique for determining formation of the complex may be used. For example, an antigen-binding molecule according to the invention, having a label associated therewith may be utilised in immunoassays. Such immunoassays include, but are not limited to, radioimmunoassays (RIAs), enzyme-linked immunosorbent assays (ELISAs) and immunochromatographic techniques (ICTs) which are well known those of skill in the art. For example, reference may be made to "CURRENT PROTOCOLS IN IMMUNOLOGY" (1994, supra) which discloses a variety of immunoassays that may be used in accordance with the present invention. Immunoassays may include competitive assays as understood in the art.

The label associated with the antigen-binding molecule may include the following:

(a) direct attachment of the label to the antigen-binding molecule;

(b) indirect attachment of the label to the antigen-binding molecule; i.e., attachment of the label to another assay reagent which subsequently binds to the antigen-binding molecule; and (c) attachment to a subsequent reaction product of the antigen-binding molecule.

The label may be selected from a group including a chromogen, a catalyst, an enzyme, a fluorochrome, a chemiluminescent molecule, a lanthanide ion such as Europium ($Eu^{34}$), a radioisotope and a direct visual label.

In the case of a direct visual label, use may be made of a colloidal metallic or non-metallic particle, a dye particle, an enzyme or a substrate, an organic polymer, a latex particle, a liposome, or other vesicle containing a signal producing substance and the like.

A large number of enzymes suitable for use as labels is disclosed in United States Patent Specifications U.S. Pat. No. 4,366,241, U.S. Pat. No. 4,843,000, and U.S. Pat. No. 4,849,338. Suitable enzyme labels useful in the present invention include alkaline phosphatase, horseradish peroxidase, luciferase, β-galactosidase, glucose oxidase, lysozyme, malate dehydrogenase and the like. The enzyme label may be used alone or in combination with a second enzyme that is in solution.

Suitable fluorochromes include, but are not limited to, fluorescein isothiocyanate (FITC), tetramethylrhodamine isothiocyanate (TRITC), R-Phycoerythrin (RPE), and Texas Red. Other exemplary fluorochromes include those discussed by Dower et al. (International Publication WO 93/06121). Reference also may be made to the fluorochromes described in U.S. Pat. Nos. 5,573,909 (Singer et al), 5,326,692 (Brinkley et al). Alternatively, reference may be made to the fluorochromes described in U.S. Pat. Nos. 5,227,487, 5,274,113, 5,405,975, 5,433,896, 5,442,045, 5,451,663, 5,453,517, 5,459,276, 5,516,864, 5,648,270 and 5,723,218.

The invention also extends to a method for detecting infection of patients by *Helicobacter*, comprising the steps of contacting a biological sample from a patient with a polypeptide, fragment, variant or derivative of the invention, and determining the presence or absence of a complex between said polypeptide, fragment, variant or derivative and *Helico-*

*bacter*-specific antibodies in said serum, wherein the presence of said complex is indicative of said infection.

In a preferred embodiment, detection of the above complex is effected by detectably modifying said polypeptide, fragment, variant or derivative with a suitable label as is well known in the art and using such modified compound in a suitable immunoassay as for example described above.

6. Compositions

A further feature of the invention is the use of the polypeptides, fragments, variants or derivatives of the invention ("immunogenic agents") as actives, together with a pharmaceutically acceptable carrier, in a composition for protecting or treating patients against *Helicobacter* infection, and preferably against *H. pylori* infection.

Depending upon the particular route of administration, a variety of pharmaceutically acceptable carriers, well known in the art may be used. These carriers may be selected from sugars, starches, cellulose and its derivatives, malt, gelatine, talc, calcium sulphate, vegetable oils, synthetic oils, polyols, alginic acid, phosphate buffered solutions, emulsifiers, isotonic saline, and pyrogen-free water.

Any suitable route of administration may be employed for providing a patient with the composition of the invention. For example, oral, rectal, parenteral, sublingual, buccal, intravenous, intra-articular, intramuscular, intra-dermal, intranasal, subcutaneous, inhalational, intraocular, intragastric, intraperitoneal, intracerebroventricular, transdermal and the like may be employed. Intra-muscular and subcutaneous injection is appropriate, for example, for administration of immunogenic compositions, vaccines and DNA vaccines. Preferably, but not essentially, the composition is administered intranasally, orally and/or intragastrically and preferably in association with a mucosal adjuvant as for example described herein.

Dosage forms include tablets, dispersions, suspensions, injections, solutions, syrups, troches, capsules, suppositories, aerosols, transdermal patches and the like. These dosage forms may also include injecting or implanting controlled releasing devices designed specifically for this purpose or other forms of implants modified to act additionally in this fashion. Controlled release of the therapeutic agent may be effected by coating the same, for example, with hydrophobic polymers including acrylic resins, waxes, higher aliphatic alcohols, polylactic and polyglycolic acids and certain cellulose derivatives such as hydroxypropylmethyl cellulose. In addition, controlled release may be effected by using other polymer matrices, liposomes and/or microspheres.

An immunogenic agent of the invention can be administered orally to the host. Compositions suitable for oral or parenteral administration may be presented as discrete units such as capsules, sachets or tablets each containing a predetermined amount of one or more immunogenic agents of the invention, as a powder or granules or as a solution or a suspension in an aqueous liquid, a non-aqueous liquid, an oil-in-water emulsion or a water-in-oil liquid emulsion Such compositions may be prepared by any of the methods of pharmacy but all methods include the step of bringing into association one or more immunogenic agents as described above with the carrier which constitutes one or more necessary ingredients. In general, the compositions are prepared by uniformly and intimately admixing the immunogenic agents of the invention with liquid carriers or finely divided solid carriers or both, and then, if necessary, shaping the product into the desired presentation.

The above compositions may be administered in a manner compatible with the dosage formulation, and in such amount as is immunogenically effective to protect or treat patients against *Helicobacter* infection. The dose administered to a patient, in the context of the present invention, should be sufficient to effect a beneficial response in a patient over time such as a reduction in the level of *Helicobacter*, or to inhibit infection by *Helicobacter*. The quantity of the immunogenic agent(s) to be administered may depend on the subject to be treated inclusive of the age, sex, weight and general health condition thereof. In this regard, precise amounts of the immunogenic agent(s) for administration will depend on the judgement of the practitioner. In determining the effective amount of the immunogenic agent to be administered in the treatment or prophylaxis against *Helicobacter*, the physician may evaluate circulating plasma levels, progression of disease, and the production of anti-Helicobacter antibodies. In any event, those of skill in the art may readily determine suitable dosages of the immunogenic agents of the invention. Such dosages may be in the order of nanograms to milligrams of the immunogenic agents of the invention.

The above compositions may be used as therapeutic or prophylactic vaccines. Accordingly, the invention extends to the production of vaccines containing as actives one or more of the immunogenic agents of the invention. Any suitable procedure is contemplated for producing such vaccines. Exemplary procedures include, for example, those described in NEW GENERATION VACCINES (1997, Levine et al., Marcel Dekker, Inc. New York, Basel Hong Kong).

An immunogenic agent according to the invention can be mixed, conjugated or fused with other antigens, including B or T cell epitopes of other antigens. In addition, it can be conjugated to a carrier as described below.

When an haptenic peptide is used (i.e., a peptide which reacts with cognate antibodies, but cannot itself elicit an immune response), it can be conjugated with an immunogenic carrier. Useful carriers are well known in the art and include for example: thyroglobulin; albumins such as human serum albumin; toxins, toxoids or any mutant crossreactive material (CRM) of the toxin from tetanus, diphtheria, pertussis, *Pseudomonas, E. coli, Staphylococcus*, and *Streptococcus*; polyamino acids such as poly(lysine:glutamic acid); influenza; Rotavirus VP6, Parvovirus VP1 and VP2; hepatitis B virus core protein; hepatitis B virus recombinant vaccine and the like. Alternatively, a fragment or epitope of a carrier protein or other immunogenic protein may be used. For example, a haptenic peptide can be coupled to a T cell epitope of a bacterial toxin, toxoid or CRM. In this regard, reference may be made to U.S. Pat. No. 5,785,973.

In addition, a polypeptide, fragment, variant or derivative of the invention may act as a carrier protein in vaccine compositions directed against *Helicobacter*, preferably against *H. pylori*, or against other bacteria or viruses.

The immunogenic agents of the invention may be administered as multivalent subunit vaccines in combination with other *Helicobacter* immunogens such as urease or the lipopolysaccharide (LPS) of *Helicobacter* bacteria (see International Patent Application No. PCT/AU95/00077). Alternatively, or additionally, they may be administered in concert with immunologically active antigens against other pathogenic species such as, for example, the pathogenic bacteria *H. influenzae, M. catarrhalis, N. gonorrhoeae, E. coli, S. pneumoniae* etc.

The vaccines can also contain a physiologically acceptable diluent or excipient such as water, phosphate buffered saline and saline.

The vaccines and immunogenic compositions may include an adjuvant as is well known in the art. Suitable adjuvants include, but are not limited to: surface active substances such as hexadecylamine, octadecylamine, octadecyl amino acid esters, lysolecithin, dimethyldioctadecylammonium bromide, N,N-dicoctadecyl-N', N'bis(2-hydroxyethyl-propanediamine), methoxyhexadecylglycerol, and pluronic polyols; polyamines such as pyran, dextransulfate, poly IC carbopol; peptides such as muramyl dipeptide and derivatives, dimethylglycine, tuftsin; oil emulsions; and mineral gels such as aluminum phosphate, aluminum hydroxide or alum; lymphokines, and QuilA.

Preferably, the adjuvant is a mucosal adjuvant. Such adjuvant is optionally, and preferably, administered with immunogenic agent(s) of the invention. Preferably, the mucosal adjuvant is cholera toxin. Mucosal adjuvants other than cholera toxin which may be used in accordance with the present invention include non-toxic derivatives of cholera toxin, such as the B sub-unit (CTB), chemically modified cholera toxin, or related proteins produced by modification of the cholera toxin amino acid sequence. These may be added to, or conjugated with, immunogenic agent(s) of the invention. The same techniques can be applied to other molecules with mucosal adjuvant or delivery properties such as *Escherichia coli* heat labile toxin. Other compounds with mucosal adjuvant or delivery activity may be used such as bile; polycations such as DEAE-dextran and polyornithine; detergents such as sodium dodecyl benzene sulphate; lipid-conjugated materials; antibiotics such as streptomycin; vitamin A; and other compounds that alter the structural or functional integrity of mucosal surfaces. Other mucosally active compounds include derivatives of microbial structures such as MDP; acridine and cimetidine.

The immunogenic agents of the invention may be delivered in ISCOMS (immune stimulating complexes), ISCOMS containing CTB, liposomes or encapsulated in compounds such as acrylates or poly(DL-lactide-co-glycoside) to form microspheres of a size suited to adsorption by M cells. Alternatively, micro or nanoparticles may be covalently attached to molecules such as vitamin B12, which have specific gut receptors. The polypeptide, fragments, variant or derivative of the invention may also be incorporated into oily emulsions and delivered orally. An extensive though not exhaustive list of adjuvants can be found in Cox and Coulter (Cox and Coulter, 1992, Advances in adjuvant technology and application. In Animal Parasite Control Using Biotechnology. Edited by W. K. Yong. Published by CRC Press).

The immunogenic agents of the invention may be expressed by attenuated viral hosts. A virus may be rendered substantially avirulent by any suitable physical (e.g., heat treatment) or chemical means (e.g., formaldehyde treatment). Ideally, the infectivity of the virus is destroyed without affecting the proteins that carry the immunogenicity of the virus. From the foregoing, it will be appreciated that attenuated viral hosts may comprise live viruses or inactivated viruses.

Attenuated viral or bacterial hosts which may be useful in a vaccine according to the invention may comprise viral vectors inclusive of adenovirus, cytomegalovirus and preferably pox viruses such as vaccinia (see for example Paoletti and Panicali, U.S. Pat. No. 4,603,112) and attenuated *Salmonella* strains (see for example Stocker, U.S. Pat. No. 4,550,081).

Live vaccines are particularly advantageous because they lead to a prolonged stimulus that can confer substantially long-lasting immunity. Thus, as an alternative to the delivery of the immunogenic agents in the form of a therapeutic or prophylactic vaccine composition, these agents may be delivered to the host using a live vaccine vector, in particular using live recombinant bacteria, viruses or other live agents, containing the genetic material necessary for the expression of the polypeptide, immunogenic fragment, variant or derivative of the invention as a foreign antigen. Particularly, bacteria that colonise the gastrointestinal tract, such as *Salmonella, Yersinia, Vibrio, Escherichia* and BCG have been developed as vaccine vectors, and these and other examples are discussed by Holmgren et al. (1992, *Immunobiol*. 184: 157-179) and McGhee et al. *Vaccine* 10(2): 75-88).

Multivalent vaccines can be prepared from one or more microorganisms that express different epitopes of *Helicobacter* (e.g., other surface proteins or epitopes of *Helicobacter*). In addition, epitopes of other pathogenic microorganisms can be incorporated into the vaccine.

In a preferred embodiment, this will involve the construction of a recombinant vaccinia virus to express a nucleic acid sequence according to the invention. Upon introduction into a host, the recombinant vaccinia virus expresses the immunogenic agent, and thereby elicits a host CTL response. For example, reference may be made to U.S. Pat. No. 4,722,848, which describes vaccinia vectors and methods useful in immunisation protocols.

A variety of other vectors useful for therapeutic administration or immunisation with the immunogenic agents of the invention will be apparent to those skilled in the art from the present disclosure.

In a further embodiment, a polynucleotide of the invention may be used as a vaccine in the form of a "naked DNA" vaccine as is known in the art. For example, an expression vector of the invention may be introduced into a mammal, where it causes production of a polypeptide in vivo, against which the host mounts an immune response as for example described in Barry, M. et al., (1995, *Nature,* 377:632-635).

7. Detection Kits

The present invention also provides kits for the detection of *Helicobacter* in a biological sample. These will contain one or more agents described above depending upon the nature of the test method employed. In this regard, the kits may include one or more of a polypeptide, fragment, variant, derivative, or antigen-binding molecule according to the invention. The kits may also optionally include appropriate reagents for detection of labels, positive and negative controls, washing solutions, dilution buffers and the like.

In order that the invention may be readily understood and put into practical effect, particular preferred embodiments will now be described by way of the following non-limiting examples.

EXAMPLES

Example 1

Preparation of a Vector Expressing a C-Terminal Portion of *H. pylori* Catalase

A full-length catalase clone derived from an *H. pylori* library clone (strain HP921023) was used as template for PCR amplification of the 3' 402 bp fragment using oligonucleotide primers as follows:

5'GCCGTATACATGCAAAACGGGTATTACGG3' (SEQ ID NO: 6) and

5'GCCAGATCTCTTTTTCTTTTTCGTGTGGTGC3' (SEQ ID NO: 7).

The resulting PCR product was cloned blunt into the TA Cloning Vector pCR2.1 (Invitrogen). It was subsequently subcloned, utilising the PCR introduced restriction sites BstZ17I and BglII, into the corresponding sites in the vector pGEXStopIV™, generating a 3' hexahistidine coding fusion.

pGEXStopIV™ is a further modified version of the vector construct, described in Edwards et al. (1998, *Recent Research Developments in Biotechnology and Bioengineering* 1: 343-356) where sequences between the EcoRI and BglII sites were removed and replaced with a new ribosome binding site and polylinker sequence using annealed oligonucleotides creating the sequence 5'GAATTCAATTAAAAATTAAGGAGG-TATACTAGTGGTACCAGATCT3' (SEQ ID NO: 8). In addition, this vector carries a Kan$^R$ cassette from pUC4k (Pharmacia Biotech) cloned into the SalI site.

The cloned catalase variant was sequenced from both strands using the commercially available 5' pGex primer (Pharmacia Biotech, 5' GGGCTGGCAAGCCACGTTTG-GTG3') (SEQ ID NO: 9) as well as a specifically synthesised oligonucleotide primer which binds the downstream Kan$^R$ gene, 5'CAGCAACACCTTCTTCACG3' (SEQ ID NO: 10). The nucleotide and deduced amino acid sequences of catalase gene fragment are set forth in SEQ ID NO: 3 and 4, respectively.

Small-scale expression (10 mL) in *E. coli* strain ER1793 was monitored over time following induction with 1 mM IPTG. Analysis by SDS-PAGE showed visible levels of induced protein of the expected size (~17 kDa), however it appeared to become increasingly truncated/degraded over time, with little remaining after overnight induction. Western blots using 11 different monoclonal antibodies raised against full-length catalase (CA5-8E3, CA5-5C2-1C7, CA5-7D2-1C2, CA5-5B2-1B8, CA5-7B8-2F3, CA5-7D7-1C3, CA5-7D7-2F4, CA5-1E10-1E11, CA5-1E9-1C3, CA5-5G7-1B7, CA5-8B8-1F3) showed the recombinant protein to be recognised by the latter four. A western blot probed with monoclonal antibody CA5-8B8-1F3 is shown in FIG. 1.

Given the apparent protein instability in ER1793, the cloned DNA was transformed into an alternative expression strain, *E. coli* BL21, which lacks 2 major proteases, OmpT and Lon. Expression in this host resulted in a far more stable product, which appeared to remain full-length after overnight induction. The BL21 transformant was used for scale-up (1 L) and protein purification, utilising the C-terminal hexahistidine tag for metal affinity chromatography. Eluted protein was dialysed against TNG (0.05 M Tris-HCl/0.5M NaCl/8% glycerol/pH7.4) to remove imidazole. It was also processed on PVDF membrane for subsequent N-terminal sequencing. The N-terminal sequence analysis of the purified protein revealed that it comprised the expected sequence of MQNGYY (SEQ ID NO: 11).

Example 2

Demonstration of the Therapeutic Efficacy of the C-Terminal Portion of *H. Pylori* Catalase Briefly, the vector of Example 1 was used to express a polypeptide consisting essentially of a C-terminal portion of *H. pylori* catalase. This polypeptide underwent extraction and purification procedures including metal affinity chromatography. The partially purified catalase fragment was then tested for therapeutic activity in two different mouse models of *Helicobacter pylori* infection (C57BL/6 and BALB/c mouse strains infected with *H. pylori* strain SS1), using two different routes of administration (intranasal and intragastric).

Vector Growth and Fragment Purification

The following method for purification of catalase fragment is based on a one liter induced culture. The method is essentially that given in the pET System Manual (Novagen).

Inoculate 100 mL TB/Kan with CSL1458 and grow @ 37° C., shaking, O/N

Subculture 1/10 into 2×500 mL TB/Kan in 2 L flasks and grow @ 37° C., shaking

At $A_{600}$~2-3, induce with 0.5 mM IPTG

Harvest cells @~5 hours post-induction and store @~80° C. if necessary

Resuspend cells in 80 mL of BB, containing Complete™ EDTA-free Protease Inhibitor Cocktail (Boehringer Mannheim)

Disrupt cells by sonication as 2×40 mL lots

Sonicate on ice, for 3 minutes total, 10 sec on/20 sec rest

Centrifuge the lysate @ 39,000×g for 20 mins to remove debris

Batch bind soluble supernatant with ~12 mL Qiagen Ni-NTA agarose slurry (=6 ml resin): 4° C., stirring, 90 min, overnight.

Load column (30 mL, Biorad), RT

Wash with 10 volumes BB (~60 mL)

Wash with 6 volumes WB (~36 mL)

Elute with EB, collect 2 mL fractions

Analyse fractions by SDS PAGE

Dialyse desired fractions stirring @ 4° C., against TNG, using Pierce Slide-A-Lyzer cassettes with 10,000 MW cut-off.

The material in the batch used for testing in mouse models of *H. pylori* infection as described below was obtained from 6.5 liters of culture, collected from a single chromatographic fraction (no. 6) at a concentration of 47.5 mg protein/mL, and purity by SDS-PAGE of approximately 70%.

Media and Buffers

TB: Terrific Broth containing 17 mM $KH_2PO_4$, 72 mM $K_2HPO_4$

Kan: Kanamycin @ 50 µg/mL

BB: 5 mM imidazole/0.5M NaCl/20 mM Tris-HCl pH7.9

WB: 60 mM imidazole/0.5M NaCl/20 mM Tris-HCl pH 7.9

EB: 1M imidazole/0.5M NaCl/20 mM Tris-HCl pH7.9

TNG: 0.05M Tris-HCl/0.5M NaCl/8% glycerol/pH7.4

Mice 80 female age-matched C57BL/6 and BALB/c mice were obtained from the Biological Resources Centre, Sydney and used at 6-8 weeks of age.

Growth of *H. pylori*-SS1 for Challenge of Mice

Aliquots of stock *H. pylori*-SS1 were maintained at −80° C. Before use, the bacteria were resuscitated by removal of stock from deep freeze and thawed at 4° C. When fully liquefied, 200 µL of suspension was aseptically distributed over the entire surface of Horse Blood Agar (HBA) plates using a sterilised glass spreader. Plates were incubated "face up" at 37° C. for 48 hours in a Steri-Cult™ 200 incubator (Selby Scientific Ltd, NSW, Australia) with 10% $CO_2$ and 95% relative humidity.

Large quantities of bacteria for challenge of mice were prepared in liquid culture. Conical flasks were prepared in advance by addition of 300 mL of Brain Heart Infusion broth (BHI) and sealed with a non-absorbent cotton wool plug. The flask was then autoclaved at 121° C. for 15 minutes followed by addition of Skirrow's antibiotic supplement (600 µL) and Fungizone (150 µL) were added aseptically and the flask loosely resealed with the plug. Two plates of resuscitated SS1 were transferred to each flask that was placed into an anaerobe jar with a gas generating kit (Anaerobic System BR38, Oxoid) and incubated at 37° C. for 48 hours with continuous gentle shaking.

Following the incubation period, the culture was examined for contamination by light microscopy and dispensed into sterile 50 mL centrifuge tubes (Sarstedt, Germany). Suspensions were centrifuged at 2500 RPM for 10 minutes and the pellets resuspended in BHI and examined under phase contrast light microscopy to confirm motility and freedom from contamination.

Bacteria were quantified under light microscopy (400×) using a haemocytometer and adjusted to approximately 108 viable organisms per mL in BHI. Mice were orogastrically challenged with 100 μL of this suspension, a volume which contained 107 organisms.

Intragastric Gavage

Challenge of mice with bacteria, plus intragastric immunisations were performed as follows. Individual mice were physically restrained by hand and immobilised by application of a firm grip about the scuff and tail. The gavage was inserted into the space between the left incisors and molars and guided in a caudal direction to the right ramus of the mandible. Passage was generally facilitated by the onset of a swallowing reflex as the gavage approached the pharynx allowing progression into the oesophagus.

The neck of the mouse was gently extended to provide a straight line between the oesophageal orifice and the cardiac sphincter. The gavage was inserted down the oesophagus into the stomach and specific aliquot delivered. The delivery device consisted of single lumen polyethylene tubing (internal diameter 0.58 mm, external diameter 0.96 mm; Critchley Electrical Products Pty Ltd, Auburn, NSW) connected to a 23 gauge hypodermic needle. The gavage needle was in turn attached to a 1-mL tuberculin syringe.

From the foregoing, however, it will be appreciated that intragastric administration is a method for delivering the formulation to the gastrointestinal tract and would be readily replaced by oral delivery in a cooperative species.

Infection of Mice

80 C57BL/6 mice and 80 BALB/c were infected intragastrically with two doses of $10^7$ $H.$ $pylori$-SS1 in 100 μL of PBS, each of the two doses being administered two days apart.

Therapeutic Immunisation

Both strains of mice were split into four groups consisting of twenty animals each (outlined below). Two groups were immunised intragastrically with either a control preparation consisting of cholera toxin adjuvant alone or the polypeptide with cholera toxin adjuvant diluted in bicarbonate in a total volume of 100 μL. For intranasal immunisations, a total volume of 10 μL was delivered using a P10 Eppendorf pipette. Intranasal preparations were also diluted in bicarbonate.

| Group (n = 20) Route | Immunisation |
|---|---|
| C57BL/6 | |
| Intragastric | 10 μg CT |
| Intragastric | 100 μg Cat fragment + 10 μg CT |
| Intranasal | 10 μg CT |
| Intranasal | 100 μg Cat fragment + 10 μg CT |
| BALB/c | |
| Intragastric | 10 μg CT |
| Intragastric | 100 μg Cat fragment + 10 μg CT |

-continued

| Group (n = 20) Route | Immunisation |
|---|---|
| Intranasal | 10 μg CT |
| Intranasal | 100 μg Cat fragment + 10 μg CT |

Five weeks after infection, four therapeutic immunisations were given at weekly intervals, according to the above table.

Collection

Five weeks after the last immunisation, the stomachs of the mice were removed and the bacterial burden in each stomach assessed by colony forming assay:

Pre-weighed stomach samples were homogenised in 2 mL of physiological saline and maintained on ice prior to plating. Samples were diluted $1:10^1$, $1:10^2$, $1:10^3$ and $1:10^4$ in saline and a 200 μl sample of each dilution distributed across GSSA plates. Plates were incubated at 37° C. for 5 days with 10% $CO_2$ and 95% relative humidity. Bacterial burden was then determined by counting the number of colonies growing.

Colony forming units were calculated per gram of stomach tissue using the following formula:

$$\text{Colony Forming Units} = \frac{\text{Number of counted colonies} \times 10^{\text{dilution factor}}}{\text{Weight of stomach tissue in grams}}$$

Buffers and Solutions

| 0.1 M Phosphate Buffered Saline | |
|---|---|
| Sodium dihydrogen orthophoshate ($NaH_2PO_4 \cdot 2H_2O$) | 4.37 g/L |
| di-Sodium Hydrogen orthophoshate, anhydrous ($Na_2HPO_4$) | 10.22 g/L |
| Sodium Chloride (NaCl) | 8.5 g/L |

Salts were dissolved in distilled $H_2O$ to 90% of total volume. The pH was adjusted to 7.2 and volume brought to specification in volumetric glassware. Solution was dispensed into appropriate glass containers and sterilised by autoclave at 121° C. and 100 Kpa for 15 minutes. The sterilised aliquots were stored at room temperature.

Horse Blood Agar

Horse blood agar (HBA) is used for the re-animation of $H.$ $pylori$ from frozen stock suspensions. Due to the non-addition of antibiotic supplements, HBA is a good indicator for the early detection of contaminants from stock cultures.

| | |
|---|---|
| Blood Agar Base No. 2 (CM271, Oxoid, Basingstoke, U.K.) | 38.0 g/L |
| Defibrillated Whole Horse Blood (Oxoid, Melbourne, Australia) | 50.0 mL/L |
| Amphotericin B (Fungizone ®, Squibb, Princetown, NJ, USA) | 2.5 mg/L |

Blood agar base powder was accurately weighed and thoroughly mixed with distilled water and adjusted to volume. The solution was dispensed into appropriate glass vessels and sterilised by autoclave at 121° C. and 100 Kpa for 15 minutes. The sterilised solution was allowed to slowly cool to 46° C. in a thermostatically controlled water bath.

Horse blood and Fungizone® were added aseptically to the media and gently mixed.

Aliquots of 20 mL were poured aseptically into sterile plastic 90-mm petri dishes (Techno-plas, SA, Australia). The plates were allowed to cool for a minimum of 1 hour then packaged tightly in polyethylene wrap to retain moisture and stored "face" up at 4° C. HBA plates were used within 1 week of manufacture.

Brain Heart Infusion Broth (BHI)

BHI broth was the medium for growth of *H. pylori* for in-vivo infection and bacterial challenge of mice.

| | |
|---|---|
| Blood Agar Base No. 2 (CM271, Oxoid, Basingstoke, U.K.) | 38.0 g/L |
| Defibrillated Whole Horse Blood (Oxoid, Melbourne, Australia) | 50.0 mL/L |
| Amphotericin B (Fungizone ®, Squibb, Princetown, NJ, USA) | 2.5 mg/L |
| Skirrow's Selective Supplement | 2.0 mL/L |

Formulation:

Brain heart infusion powder was accurately weighed and thoroughly mixed with distilled water and adjusted to volume. Three hundred mL aliquots of dissolved BHI were dispensed into 1 liter glass conical flasks and sealed with a non-absorbent cotton wool bung and tops covered with aluminium foil secured by autoclave tape, then sterilised by autoclave at 121° C. and 100 Kpa for 15 minutes. Prepared flasks (excluding serum and antibiotics) were stored at room temperature with a shelf life of 4 weeks maximum.

| Skirrow's Selective Supplement | |
|---|---|
| Vancomycin HCl (Eli Lilly & Co, West Ryde, Australia) | 5 mg/mL |
| Polymyxin B Sulfate (Sigma, St Louis, MO, USA) | 1250 U/mL |
| Trimethoprim (Sigma) | 2.5 mg/mL |

Formulation:

Trimethoprim was dissolved in minimal 95% ethanol. Vancomycin and Polymyxin B were added and adjusted to volume in sterile distilled water. The solution was filter sterilised (0.22 µm Minisart®, Sartorius, VIC, Australia) into desired aliquots, and stored at −20° C.

| Campylobacter Selective Agar (CSA) | |
|---|---|
| Blood Agar Base No. 2 (CM271, Oxoid, Basingstoke, U.K.) | 38.0 g/L |
| Defibrillated Whole Horse Blood (Oxoid, Melbourne, Australia) | 50.0 mL/L |
| Amphotericin B (Fungizone ®, Squibb, Princetown, NJ, USA) | 2.5 mg/L |
| Skirrow's Selective Supplement | 2.0 mL/L |

Formulation:

Blood agar base powder was accurately weighed and thoroughly mixed with distilled water and adjusted to volume. The solution was dispensed into appropriate glass vessels and sterilised by autoclave at 121° C. and 100 Kpa for 15 minutes. The sterilised solution was allowed cool to 46° C. in a thermostatically controlled water bath.

Horse blood, Skirrow's selective supplement and Fungizone® were added aseptically to the media and gently mixed. Aliquots of 20 mL were poured aseptically into sterile plastic 90 mm Petri dishes (Techno-plas™, SA, Australia). The plates were allowed to set then packaged tightly in polyethylene wrap to retain moisture and stored at 4° C. CSA plates were used within 1 week of manufacture.

| Physiological Saline | |
|---|---|
| Sodium Chloride (NaCl) | 8.5 g/L |

Formulation:

Sodium chloride was accurately weighed and dissolved in distilled $H_2O$ to 90% of total volume. The pH was adjusted to 7.0 and volume brought to specification in volumetric glassware. Solution was dispensed into appropriate glass containers and sterilised by autoclave at 121° C. and 100 Kpa for 15 minutes. The sterilised aliquots were stored at room temperature.

Glaxo Selective Supplement Agar (GSSA)

Glaxo Selective Supplement Agar (GSSA) is a highly selective media, used for the culture and recognition of colony forming units of *H. pylori* as an assay of in vivo bacterial load.

| | |
|---|---|
| Blood Agar Base No. 2 (CM271, Oxoid, Basingstoke, U.K.) | 38.0 g/L |
| Defibrillated Whole Horse Blood (Oxoid, Melbourne, Australia) | 50.0 mL/L |
| Amphotericin B (Fungizone ®, Squibb, Princetown, NJ, USA) | 2.5 mg/L |
| Glaxo Selective Supplement A | 1.5 mL/L |
| Glaxo Selective Supplement B | 500 µL/L |

Formulation:

Blood agar base powder was accurately weighed and thoroughly mixed with distilled water and adjusted to volume. The solution was dispensed into appropriate glass vessels and sterilised by autoclave at 121° C. and 100 Kpa for 15 minutes. The sterilised solution was allowed cool to 46° C. in a thermostatically controlled water bath.

Horse blood, selective antibiotics and Fungizone® were added aseptically to the media and gently mixed. Aliquots of 20 mL were poured aseptically into sterile plastic 90 mm Petri dishes (Techno-plas™, SA, Australia). The plates were allowed to set then packaged tightly in polyethylene wrap to retain moisture and stored "face" up at 4° C. GSSA plates were used within 1 week of manufacture.

Results

The results, shown in TABLES 1-4, are expressed as colony forming units (c.f.u.) per mL per gram of gastric tissue, calculated as described above. The control group and the test group are shown for each of the four combinations tested: (1) C57BL/6 immunised intranasally; (2) C57BL/6 immunised intragastrically; (3) BALB/c immunised intranasally; and BALB/c immunised intragastrically.

TABLE 1

| C57BL/6 Intranasal | | | |
|---|---|---|---|
| CT (Negative control) | | Catalase fragment | |
| Mouse no. | C.F.U./g (×$10^6$) | Mouse no. | C.F.U./g (×$10^6$) |
| 1 | 1.685 | 1 | 0.092 |
| 2 | 3.603 | 2 | 0.196 |
| 3 | 10.241 | 3 | 0.256 |
| 4 | 1.392 | 4 | 0.045 |

TABLE 1-continued

C57BL/6 Intranasal

| CT (Negative control) | | Catalase fragment | |
|---|---|---|---|
| Mouse no. | C.F.U./g ($\times 10^6$) | Mouse no. | C.F.U./g ($\times 10^6$) |
| 5 | 18.182 | 5 | 0.163 |
| 6 | 1.283 | 6 | 0.013 |
| 7 | 14.384 | 7 | 0.107 |
| 8 | 1.503 | 8 | 0.044 |
| 9 | 14.65 | 9 | 0.315 |
| 10 | 3.278 | 10 | 0.357 |
| 11 | 3.02 | 11 | 0.23 |
| 12 | 9.009 | 12 | 0.146 |
| 13 | 10.909 | 13 | 1.667 |
| 14 | 1.667 | 14 | 0.296 |
| 15 | 1.779 | 15 | 0.062 |
| 16 | 13.918 | 16 | 0.494 |
| 17 | 4.795 | 17 | 0.124 |
| | | 18 | 0.066 |
| | | 19 | 0.32 |
| | | 20 | 0.151 |

TABLE 2

C57BL/6 Intragastric

| CT (Negative control) | | Catalase fragment | |
|---|---|---|---|
| Mouse no. | C.F.U./g ($\times 10^6$) | Mouse no. | C.F.U./g ($\times 10^6$) |
| 1 | 2.24 | 1 | 0.263 |
| 2 | 2.34 | 2 | 0.056 |
| 3 | 2.5 | 3 | 1.193 |
| 4 | 1.89 | 4 | 1.284 |
| 5 | 1.69 | 5 | 0.463 |
| 6 | 2.45 | 6 | 1.627 |
| 7 | 2.36 | 7 | 0.831 |
| 8 | 1.86 | 8 | 1.733 |
| 9 | 3.54 | 9 | 0.451 |
| 10 | 1.94 | 10 | 2.989 |
| 11 | 3.33 | 11 | 0.253 |
| 12 | 2.55 | 12 | 0.853 |
| 13 | 3.1 | 13 | 1.533 |
| 14 | 3.18 | 14 | 0.176 |
| 15 | 2.27 | 15 | 2.167 |
| 16 | 3.06 | 16 | 1.384 |
| 17 | 1.69 | 17 | 0.548 |
| 18 | 2.64 | 18 | 1.329 |
| 19 | 2.85 | 19 | 0.463 |
| 20 | 2.86 | | |

TABLE 3

BALB/c Intranasal

| CT (Negative control) | | Catalase fragment | |
|---|---|---|---|
| Mouse no. | C.F.U./g ($\times 10^6$) | Mouse no. | C.F.U./g ($\times 10^6$) |
| 1 | 0.223 | 1 | 0.053 |
| 2 | 0.199 | 2 | 0.078 |
| 3 | 0.197 | 3 | 0.189 |
| 4 | 1.448 | 4 | 0.016 |
| 5 | 0.482 | 5 | 0.249 |
| 6 | 0.243 | 6 | 0.087 |
| 7 | 0.337 | 7 | 0.024 |
| 8 | 0.226 | 8 | 0.013 |
| 9 | 0.338 | 9 | 0.186 |
| 10 | 0.206 | 10 | 0.012 |
| 11 | 0.172 | 11 | 0.142 |
| 12 | 0.396 | 12 | 0.014 |
| 13 | 0.171 | 13 | 0.215 |
| 14 | 0.21 | 14 | 0.06 |
| 15 | 0.184 | 15 | 0.041 |
| 16 | 0.207 | 16 | 0.047 |
| 17 | 0.214 | 17 | 0.028 |
| 18 | 1.029 | 18 | 0.274 |
| 19 | 1.854 | 19 | 0.03 |
| 20 | 3.371 | | |

TABLE 4

BALB/c Intragastric

| CT (Negative control) | | Catalase fragment | |
|---|---|---|---|
| Mouse no. | C.F.U./g ($\times 10^6$) | Mouse no. | C.F.U./g ($\times 10^6$) |
| 1 | 0.479 | 1 | 0.09 |
| 2 | 0.22 | 2 | 0.14 |
| 3 | 0.248 | 3 | 0.024 |
| 4 | 0.467 | 4 | 0.061 |
| 5 | 0.251 | 5 | 0.023 |
| 6 | 0.601 | 6 | 0.192 |
| 7 | 0.306 | 7 | 0.128 |
| 8 | 1.342 | 8 | 0.177 |
| 9 | 1.543 | 9 | 0.061 |
| 10 | 0.297 | 10 | 0.185 |
| 11 | 0.444 | 11 | 0.11 |
| 12 | 0.184 | 12 | 0.054 |
| 13 | 0.13 | 13 | 0.297 |
| 14 | 1.104 | 14 | 0.068 |
| 15 | 1.047 | 15 | 0.242 |
| 16 | 0.257 | 16 | 0.23 |
| 17 | 0.568 | 17 | 0.139 |
| 18 | 0.264 | 18 | 0.235 |
| 19 | 0.143 | 19 | 0.233 |
| 20 | 2.483 | | |

Analysis of Data Sets

T-tests were performed on log-transformed data. TABLE 5 summarises the results for the t-tests on the log-transformed data:

TABLE 5

| Strain | Route | t-statistic | df | P-value |
|---|---|---|---|---|
| C57B-6 | Intranasal | 10.098 | 35 | <0.0001 |
| C57B-6 | Intragastric | 5.36 | 37 | <0.0001 |
| BALB/c | Intranasal | 5.862 | 37 | <0.0001 |
| BALB/c | Intragastric | 5.269 | 37 | <0.0001 |

Therefore, by two different routes, in two different mouse strains, administration of an immunologically effective amount of the catalase fragment polypeptide caused a significant reduction in the level of *Helicobacter pylori* infection in the treated group.

All references patents and patent applications referred to in this specification are incorporated herein by reference in their entirety.

Throughout the specification, the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appendant claims.

The invention claimed is:

1. An isolated polypeptide consisting of a sequence selected from the group consisting of SEQ ID NO:2 and SEQ ID NO:4.

2. A method for treating or preventing *Helicobacter* infection in a mammalian host, comprising administering to said host an immunogenically effective amount of a polypeptide according to claim 1.

3. The method of claim 2, wherein the polypeptide is administered in association with an adjuvant.

4. The method of claim 3, wherein the adjuvant is a mucosal adjuvant.

5. The method of claim 2, wherein the polypeptide is administered intranasally.

6. The method of claim 2, wherein the polypeptide is administered orally.

7. The method of claim 2, wherein the polypeptide is administered intragastrically.

8. The method of claim 2, wherein said host is a human.

9. A recombinant polypeptide prepared by expressing in a host cell a polynucleotide encoding a polypeptide consisting of a sequence selected from the group consisting of SEQ ID NO:2 and SEQ ID NO:4.

10. The polypeptide of claim 1, wherein said sequence is SEQ ID NO:2.

11. The polypeptide of claim 1, wherein said sequence is SEQ ID NO:4.

12. The method of claim 2, wherein said sequence is SEQ ID NO:2.

13. The method of claim 2, wherein said sequence is SEQ ID NO:4.

14. The recombinant polypeptide of claim 9, wherein said sequence is SEQ ID NO:2.

15. The recombinant polypeptide of claim 9, wherein said sequence is SEQ ID NO:4.

* * * * *

SEQUENCE LISTING

<160> NUMBER OF SEQ ID NOS: 11

<210> SEQ ID NO 1
<211> LENGTH: 405
<212> TYPE: DNA
<213> ORGANISM: Helicobacter pylori
<220> FEATURE:
<221> NAME/KEY: CDS
<222> LOCATION: (1)..(405)

<400> SEQUENCE: 1

| atg | caa | aac | gga | tac | tac | ggc | tct | tta | caa | aac | tat | acg | cct | agc | tca | 48 |
| Met | Gln | Asn | Gly | Tyr | Tyr | Gly | Ser | Leu | Gln | Asn | Tyr | Thr | Pro | Ser | Ser | |
| 1 | | | | 5 | | | | | 10 | | | | | 15 | | |

| ttg | cca | ggt | tat | aaa | gaa | gat | aag | agc | gcg | aga | gat | cct | aag | ttc | aac | 96 |
| Leu | Pro | Gly | Tyr | Lys | Glu | Asp | Lys | Ser | Ala | Arg | Asp | Pro | Lys | Phe | Asn | |
| | | | 20 | | | | | 25 | | | | | 30 | | | |

| tta | gct | cat | att | gag | aaa | gag | ttt | gaa | gtg | tgg | aat | tgg | gat | tac | agg | 144 |
| Leu | Ala | His | Ile | Glu | Lys | Glu | Phe | Glu | Val | Trp | Asn | Trp | Asp | Tyr | Arg | |
| | | 35 | | | | | 40 | | | | | 45 | | | | |

| gct | gat | gat | agc | gat | tac | tac | acc | caa | cca | ggt | gat | tac | tac | cgc | tca | 192 |
| Ala | Asp | Asp | Ser | Asp | Tyr | Tyr | Thr | Gln | Pro | Gly | Asp | Tyr | Tyr | Arg | Ser | |
| 50 | | | | | 55 | | | | | 60 | | | | | | |

| ttg | cca | gct | gat | gaa | aaa | gaa | agg | ttg | cat | gac | act | att | gga | gag | tct | 240 |
| Leu | Pro | Ala | Asp | Glu | Lys | Glu | Arg | Leu | His | Asp | Thr | Ile | Gly | Glu | Ser | |
| 65 | | | | | 70 | | | | | 75 | | | | | 80 | |

| ttg | gct | cat | gtt | acc | cat | aag | gaa | att | gtg | gat | aaa | caa | ttg | gag | cat | 288 |
| Leu | Ala | His | Val | Thr | His | Lys | Glu | Ile | Val | Asp | Lys | Gln | Leu | Glu | His | |
| | | | | 85 | | | | | 90 | | | | | 95 | | |

| ttc | aag | aaa | gct | gat | ccc | aaa | tac | gct | gag | gga | gtt | aaa | aaa | gct | ctt | 336 |
| Phe | Lys | Lys | Ala | Asp | Pro | Lys | Tyr | Ala | Glu | Gly | Val | Lys | Lys | Ala | Leu | |
| | | | 100 | | | | | 105 | | | | | 110 | | | |

| gaa | aaa | cac | caa | aag | atg | atg | aaa | gac | atg | cat | gga | aaa | gac | atg | cac | 384 |
| Glu | Lys | His | Gln | Lys | Met | Met | Lys | Asp | Met | His | Gly | Lys | Asp | Met | His | |
| | | 115 | | | | | 120 | | | | | 125 | | | | |

| cac | aca | aaa | aag | aaa | aag | taa | | | | | | | | | | 405 |
| His | Thr | Lys | Lys | Lys | Lys | | | | | | | | | | | |
| | | 130 | | | | | | | | | | | | | | |

<210> SEQ ID NO 2
<211> LENGTH: 134
<212> TYPE: PRT
<213> ORGANISM: Helicobacter pylori

<400> SEQUENCE: 2

Met Gln Asn Gly Tyr Tyr Gly Ser Leu Gln Asn Tyr Thr Pro Ser Ser
 1               5                  10                  15

Leu Pro Gly Tyr Lys Glu Asp Lys Ser Ala Arg Asp Pro Lys Phe Asn
            20                  25                  30

Leu Ala His Ile Glu Lys Glu Phe Glu Val Trp Asn Trp Asp Tyr Arg
        35                  40                  45

Ala Asp Asp Ser Asp Tyr Tyr Thr Gln Pro Gly Asp Tyr Tyr Arg Ser
 50                  55                  60

Leu Pro Ala Asp Glu Lys Glu Arg Leu His Asp Thr Ile Gly Glu Ser
 65                  70                  75                  80

Leu Ala His Val Thr His Lys Glu Ile Val Asp Lys Gln Leu Glu His
                85                  90                  95

Phe Lys Lys Ala Asp Pro Lys Tyr Ala Glu Gly Val Lys Lys Ala Leu
            100                 105                 110

```
        Glu Lys His Gln Lys Met Met Lys Asp Met His Gly Lys Asp Met His
                    115                 120                 125

His Thr Lys Lys Lys Lys
                130

<210> SEQ ID NO 3
<211> LENGTH: 405
<212> TYPE: DNA
<213> ORGANISM: Helicobacter pylori
<220> FEATURE:
<221> NAME/KEY: CDS
<222> LOCATION: (1)..(405)

<400> SEQUENCE: 3 atg caa aac ggg tat tac ggc tct tta caa aac tat acg cct agc tca        48
Met Gln Asn Gly Tyr Tyr Gly Ser Leu Gln Asn Tyr Thr Pro Ser Ser
  1               5                  10                  15 ttg cct ggc tat aaa gaa gat aag agt gca agg gat cct aag ttc aac        96
Leu Pro Gly Tyr Lys Glu Asp Lys Ser Ala Arg Asp Pro Lys Phe Asn
             20                  25                  30 tta gct cat att gag aaa gag ttt gaa gtg tgg aat tgg gat tac aga       144
Leu Ala His Ile Glu Lys Glu Phe Glu Val Trp Asn Trp Asp Tyr Arg
         35                  40                  45 gct gag gat agc gat tac tac acc caa cca ggt gat tac tac cgc tca       192
Ala Glu Asp Ser Asp Tyr Tyr Thr Gln Pro Gly Asp Tyr Tyr Arg Ser
 50                  55                  60 ttg cca gct gat gaa aaa gaa agg ttg cat gac act att gga gag tct       240
Leu Pro Ala Asp Glu Lys Glu Arg Leu His Asp Thr Ile Gly Glu Ser
 65                  70                  75                  80 tta gct cat gtt acc cat aag gaa att gtg gat aaa caa ttg gag cat       288
Leu Ala His Val Thr His Lys Glu Ile Val Asp Lys Gln Leu Glu His
                 85                  90                  95 ttc aag aaa gct gac ccc aaa tac gct gag gga gtt aaa aaa gct ctt       336
Phe Lys Lys Ala Asp Pro Lys Tyr Ala Glu Gly Val Lys Lys Ala Leu
            100                 105                 110 gaa aaa cac caa aaa atg atg aaa gac atg cat gga aaa gac atg cac       384
Glu Lys His Gln Lys Met Met Lys Asp Met His Gly Lys Asp Met His
        115                 120                 125 cac acg aaa aag aaa aag taa                                           405
His Thr Lys Lys Lys Lys
    130

<210> SEQ ID NO 4
<211> LENGTH: 134
<212> TYPE: PRT
<213> ORGANISM: Helicobacter pylori

<400> SEQUENCE: 4

Met Gln Asn Gly Tyr Tyr Gly Ser Leu Gln Asn Tyr Thr Pro Ser Ser
  1               5                  10                  15

Leu Pro Gly Tyr Lys Glu Asp Lys Ser Ala Arg Asp Pro Lys Phe Asn
             20                  25                  30

Leu Ala His Ile Glu Lys Glu Phe Glu Val Trp Asn Trp Asp Tyr Arg
         35                  40                  45

Ala Glu Asp Ser Asp Tyr Tyr Thr Gln Pro Gly Asp Tyr Tyr Arg Ser
 50                  55                  60

Leu Pro Ala Asp Glu Lys Glu Arg Leu His Asp Thr Ile Gly Glu Ser
 65                  70                  75                  80

Leu Ala His Val Thr His Lys Glu Ile Val Asp Lys Gln Leu Glu His
                 85                  90                  95
```

```
Phe Lys Lys Ala Asp Pro Lys Tyr Ala Glu Gly Val Lys Lys Ala Leu
            100                 105                 110

Glu Lys His Gln Lys Met Met Lys Asp Met His Gly Lys Asp Met His
        115                 120                 125

His Thr Lys Lys Lys Lys
    130

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: 6X His tag

<400> SEQUENCE: 5

His His His His His His
 1               5

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gccgtataca tgcaaaacgg gtattacgg                                    29

<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gccagatctc tttttctttt tcgtgtggtg c                                 31

<210> SEQ ID NO 8
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gaattcaatt aaaaattaag gaggtatact agtggtacca gatct                  45

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 9
gggctggcaa gccacgtttg gtg                                          23

<210> SEQ ID NO 10
<211> LENGTH: 19
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide

<400> SEQUENCE: 10
cagcaacacc ttcttcacg                                                    19

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Met Gln Asn Gly Tyr Tyr
 1               5
```